US008748587B2

(12) United States Patent
Gaither et al.

(10) Patent No.: US 8,748,587 B2
(45) Date of Patent: Jun. 10, 2014

(54) MOLECULES AND METHODS FOR MODULATING TMEM16A ACTIVITIES

(75) Inventors: Larry Alexander Gaither, Bradford, MA (US); Christopher John Rothwell, Swampscott, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/485,311

(22) Filed: May 31, 2012

(65) Prior Publication Data

US 2012/0308582 A1 Dec. 6, 2012

Related U.S. Application Data

(60) Provisional application No. 61/492,653, filed on Jun. 2, 2011.

(51) Int. Cl.
*C07K 16/30* (2006.01)
*C07K 16/46* (2006.01)
*A61K 39/395* (2006.01)

(52) U.S. Cl.
USPC ............... 530/388.8; 530/387.3; 530/391.7; 424/155.1; 424/183.1

(58) Field of Classification Search
CPC ............... C07K 16/30; C07K 2317/73; C07K 2317/77; C07K 7/06; C07K 7/08
See application file for complete search history.

(56) References Cited

U.S. PATENT DOCUMENTS

| | | | |
|---|---|---|---|
| 8,227,199 B2 | 7/2012 | Urech et al. | |
| 8,399,625 B1 * | 3/2013 | Escher | 530/387.3 |
| 2006/0040292 A1 | 2/2006 | West et al. | |
| 2009/0138977 A1 | 5/2009 | Domon et al. | |
| 2010/0209934 A1 | 8/2010 | Oh et al. | |
| 2011/0015239 A1 | 1/2011 | Verkman et al. | |
| 2012/0196827 A1 | 8/2012 | Van Criekinge et al. | |

FOREIGN PATENT DOCUMENTS

| | | |
|---|---|---|
| CN | 102154482 A | 8/2011 |
| WO | 02/103320 A2 | 12/2002 |

OTHER PUBLICATIONS

Zhu et al., J Physiol 2009; 587.20:4905-18.*
ab64508 data sheet, available at www.abcam.com/TMEM16A-antibody-SP31-ab64085.html, last accessed Jun. 19, 2013.*
Caputo, Antonella et al., "TMEM16A A Membrane Protein Associated with Calcium-Dependent Chloride Channel Activity", Science, vol. 322, pp. 590-594, 2008.
Carles, A. et al., "Head and neck squamous cell carcinoma transcriptome analysis by comprehensive validated differential display", Oncogene, vol. 25, pp. 1821-1831, 2006.
Carneiro, Ana et al., "Prognostic Impact of Array-based Genomic Profiles in Esophageal Squamous Cell Cancer", BMC Cancer, vol. 8, Iss. 98, 2008.
Duvvuri, Umamaheswar et al., "TMEM16A, induces MAPK and contributes directly to tumorigenesis and cancer progression", Cancer Research, 2012.
Espinosa, Ingo et al., "A Novel Monoclonal Antibody Against DOG1 is a Sensitive and Specific Marker for Gastrointestinal Stromal Tumors", Am J Surg Pathol, vol. 32, No. 2, pp. 210-218, 2008.
Galietta, Luis J. V., "The TMEM16 Protein Family: A New Class of Chloride Channels?", Biophysical Journal, vol. 97, pp. 3047-3053, 2009.
Hartzell, H. Criss et al., "Anoctamin/TMEM16 family members are Ca2+-activated Cl- channels", J Physiol, vol. 587, No. 10, pp. 2127-2139, 2009.
Huang, Xin et al., "Comprehensive Genome and Transcriptome Analysis of the llq13 Amplicon in Human Oral Cancer and Synteny to the 7F5 Amplicon in Murine Oral Carcinoma", Genes, Chromosomes & Cancer, vol. 45, pp. 1058-1069, 2006.
Kashyap, Manoj Kumar et al., "Genomewide mRNA profiling of esophageal squamous cell carcinoma for identification of cancer biomarkers" Cancer Biology & Therapy, vol. 8, Iss. 1, pp. 1-11, 2009.
Katoh, Masuko et al., "FLJ10261 gene, located within the CCND1-EMS1 locus on human chromosome 11q13, encodes the eight-transmembrane protein homologous to C12orf3, C11orf25 and FLJ34272 gene products", International Journal of Oncology, vol. 22, pp. 1375-1381, 2003.
Liegl, Bernadette et al., "Monoclonal Antibody DOG1.1 Shows Higher Sensitivity Than KIT in the Diagnosis of Gastrointestinal Stromal Tumors, Including Unusual Subtypes", Am J Surg Pathol, vol. 33, No. 3, pp. 437-446, 2009.
West, Robert B. et al., "The Novel Marker, DOG1, Is Expresse Ubiquitously in Gastrointestinal Stromal Tumors Irrespective of KIT or PDGFRA Mutation Status", American Journal of Pathology, vol. 165, No. 1, pp. 107-113, 2004.
Yang, Young Duk et al., "TMEM16A confers receptor-activated calcium-dependent chloride conductance", Nature, vol. 455, pp. 1210-1216, 2008.

* cited by examiner

*Primary Examiner* — Sheela J Huff
*Assistant Examiner* — Jessica H Roark
(74) *Attorney, Agent, or Firm* — Mei Benni

(57) ABSTRACT

The present invention provides molecules that bind to TMEM16A ("TMEM16A binding molecules"), particularly human or humanized antibodies and antibody drug conjugates that bind to human TMEM16A and modulate its functions. Epitopes of TMEM16A and molecules that bind these epitopes are also provided herein.

10 Claims, 6 Drawing Sheets

MOLECULES AND METHODS FOR MODULATING TMEM16A ACTIVITIES

FIELD OF THE INVENTION

The present invention relates to antigen binding molecules to TMEM16A, epitopes bound by those molecules, and methods of using the molecules.

BACKGROUND OF THE INVENTION

TMEM16A has been identified as a calcium activated chloride channel (see, e.g., Yang et al., Nature, 455:1210-1215 (2008)). It is also known by some other names, such as ANO1, TAOS2, ORAOV2, and DOG-1. TMEM16A belongs to the anoctamin/TMEM16 family of membrane proteins. This family includes other members, such as TMEM16B-K. All TMEM16 proteins have similar putative topology, consisting of eight transmembrane segments and cytosolic N- and C-termini (see, e.g., Galietta, Biophysical J. 97:3047-3053, (2009)).

Calcium activated chloride channels functions in many physiological processes, including transepithelial secretion, cardiac and neuronal excitation, sensory transduction, smooth muscle contraction, and fertilization. TMEM16A is potentially involved in epithelial fluid secretion, olfactory and phototransduction, neuronal and cardiac excitability, and regulation of vascular tone including gut motility (see, e.g., Galietta, 2009).

TMEM16A is also highly over expressed in some cancers, for example, gastrointestinal stromal tumor ("GIST"), and head and neck cancer. TMEM16A is located on chromosome 11q13 and it appears that amplification of this chromosomal region occurs in many tumors including almost half of oral squamous cell carcinomas (Huang et al., Genes Chromosomes Cancer 45:1058-1069, (2006)), and neck squamous cell carcinomas (Cares et al., Oncogene 25:1821-1831, (2006)).

GIST is the most common mesenchymal tumor found in the gastrointestinal tract. There is a high unmet medical need due to refractory, metastatic or resistant GIST. There is also a high unmet medical need to other cancers in which TMEM16A has been implicated.

BRIEF SUMMARY OF THE INVENTION

The present invention provides molecules that bind to TMEM16A ("TMEM16A binding molecules"), particularly TMEM16A binding molecules that specifically bind to the extracellular domain 2 ("ECD2") of TMEM16A and internalize upon binding. In some embodiments, the TMEM16A binding molecules specifically bind to a peptide comprising or consisting of amino acids KLIRYKLKLQ (SEQ ID NO: 3), or a portion thereof. In some embodiments, the TMEM16A binding molecules are human or humanized antibodies, antibody fragments, and antibody drug conjugates ("ADC"). The present invention further provides an antigenic peptide comprising or consisting of an amino acid sequence that is at least 60%, at least 70%, at least 80%, at least 90%, or 100% identical to KLIRYKLKLQ (SEQ ID NO:3), and uses thereof.

In one embodiment, the present invention provides TMEM16A binding molecules comprising an antigen binding portion of an antibody that specifically binds to TMEM16A, wherein the antigen binding portion binds to (1) a peptide comprising or consisting of an amino acid sequence that is at least 60%, at least 70%, at least 80%, at least 90%, or 100% identical to KLIRYKLKLQ (SEQ ID NO:3); and (2) extracellular domain 2 ("ECD2") of TMEME16A comprising SEQ ID NO: 3.

In one embodiment, the TMEM16A binding molecules of the invention specifically bind to an epitope on TMEM16A that comprises or consists of an amino acid sequence that is at least 60%, at least 70%, at least 80%, at least 90%, or 100% identical to KLIRYKLKLQ (SEQ ID NO:3), or a portion thereof.

In one embodiment, the TMEM16A binding molecules of the invention comprise a Fab fragment, an Fab' fragment, an F(ab')$_2$, or an Fv fragment of an antibody. In some embodiments, the TMEM16A binding molecules of the invention are a diabody or multivalent antibody comprising at least one antigen binding fragment that specifically binds to ECD2 of TMEM16A and internalize upon such binding. In some embodiments, the TMEM16A binding molecules of the invention are a diabody or multivalent antibody comprising at least one antigen binding fragment that specifically bind to a peptide comprising or consisting of an amino acid sequence that is at least 60%, at least 70%, at least 80%, at least 90%, or 100% identical to SEQ ID NO:3.

In some embodiments, the TMEM16A binding molecules of the invention are monoclonal antibodies. In some embodiments, the TMEM16A binding molecules of the invention are human or humanized monoclonal antibodies. Yet in some embodiments, the TMEM16A binding molecules of the invention are chimeric antibodies.

In some embodiments, the TMEM16A binding molecules of the invention are antibody drug conjugates, wherein the TMEM16 binding molecules are antibodies (or antigen binding fragments thereof) linked to a therapeutic moiety (e.g., a cytotoxic agent, an anti-cancer agent).

In one embodiment, the antibodies (or antigen binding fragments thereof) are linked to a therapeutic moiety (e.g., a cytotoxic agent, an anti-cancer agent) via a linker. In another embodiment, the antibodies (or antigen binding fragments thereof) are directly linked to a therapeutic moiety (e.g., a cytotoxic agent, an anti-cancer agent).

The present invention further provides pharmaceutical compositions comprising the TMEM16A binding molecules of the invention.

The present invention also provides methods of treating cancer comprising administering to a subject thereof a composition comprising therapeutically effective amount of the TMEM16A binding molecules of the invention. In some embodiments, the present invention provides a composition comprising a TMEM16A binding molecule of the invention for use in treating cancer in an individual.

In some embodiments, the present invention provides methods of treating cancer that is selected from the group consisting of gastrointestinal cancer, gastrointestinal stromal tumor, tumors of mesenchymal, epithelia, and stromal origin, esophageal squamous cell carcinoma, oral squamous cell carcinoma, cancers of the head and neck, and all cancers containing the 11q13 amplification, comprising administering to a subject in need thereof a composition comprising therapeutically effective amount of the TMEM16A binding molecules of the invention. In some embodiments, the present invention provides a composition comprising a TMEM16A binding molecule of the invention for use in treating cancer that is selected from the group consisting of gastrointestinal cancer, gastrointestinal stromal tumor, tumors of mesenchymal, epithelia, and stromal origin, esophageal squamous cell carcinoma, oral squamous cell carcinoma, cancers of the head and neck, and all cancers containing the 11q13 amplification.

With respect to embodiments of the methods and medical uses, in some embodiments, a TMEM16A binding molecule of the invention is co-administered with one or more other agents. Optionally, a TMEM16A binding molecule of the invention and a second agent are provided as a mixture. Optionally, a TMEM16A binding molecule of the invention and a second agent are provided in separate formulations.

Definitions

An "antibody" refers to a polypeptide of the immunoglobulin family that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used in this application, an "antibody" encompasses all variations of antibodies that possess a particular binding specifically, e.g., for TMEM16A. Thus, within the scope of this concept are, e.g., full length antibodies, chimeric antibodies, and humanized antibodies, and multimeric versions of these antibody fragments (e.g., multispecific, including bispecific, antibodies; multivalent antibodies) with the same binding specificity.

Antibodies exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab' which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. Paul, *Fundamental Immunology* 3d ed. (1993). While various antibody fragments are defined in terms of the digestion of an intact antibody, one of skill will appreciate that such fragments may be synthesized de novo either chemically or by using recombinant DNA methodology. As used in this application, an "antibody fragment" encompasses all variations of antibody fragments that possess a particular binding specifically, e.g., for TMEM16A. Thus, within the scope of this concept are, e.g., single chain antibodies (ScFv), Fab, Fab', and multimeric versions of these fragments (e.g., F(ab')$_2$,).

An "antibody light chain" or an "antibody heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions. In this application, antibody light chains and/or antibody heavy chains may, from time to time, be collectively referred to as "antibody chains." These terms encompass antibody chains containing mutations that do not disrupt the basic structure of $V_L$ or $V_H$, as one skilled in the art will readily recognize.

The term "antigen binding portion" of an antibody, as used herein, refers to one or more fragments of an intact antibody that retain the ability to specifically bind to a given antigen (e.g., TEMEM16A). Antigen binding functions of an antibody can be performed by fragments of an intact antibody. Examples of binding fragments encompassed within the term "antigen binding portion" of an antibody include a Fab fragment, a monovalent fragment consisting of the $V_L$, $V_H$, CL and CH1 domains; an F(ab)$_2$ fragment, a bivalent fragment comprising two Fab fragments (generally one from a heavy chain and one from a light chain) linked by a disulfide bridge at the hinge region; an Fd fragment consisting of the $V_H$ and CH1 domains; an Fv fragment consisting of the $V_L$ and $V_H$ domains of a single arm of an antibody; a single domain antibody (dAb) fragment (Ward et al., 1989 Nature 341:544-546), which consists of a $V_H$ domain; and an isolated complementarity determining region (CDR). As used herein, an "antigen-binding portion" of a TMEM16A binding molecule refers to the portion of a TMEM16A binding molecule that is responsible for the specific binding between the molecule and TMEM16A. There are at least one such antigen binding portion present in each TMEM16A binding molecule of the invention, and each of the antigen binding portion may be identical or different from the others. As used herein, the term "TMEM16A binding molecule" refers to any molecule (including antibodies, antibody fragments and antibody drug conjugates (ADCs)) that specifically bind to TMEM16A.

Furthermore, although the two domains of the Fv fragment, $V_L$ and $V_H$, are coded for by separate genes, they can be joined, using recombinant methods, by an artificial peptide linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies.

Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding portions can be incorporated into single chain molecules comprising a pair of tandem Fv segments ($V_H$-CH$_1$— $V_H$-CH$_1$) which, together with complementary light chain polypeptides, form a pair of antigen binding regions (Zapata et al., 1995 Protein Eng. 8(10):1057-1062; and U.S. Pat. No. 5,641,870).

"Complementarity-determining domains" or "complementary-determining regions" ("CDRs") interchangeably refer to the hypervariable regions of $V_L$ and $V_H$. The CDRs are the target protein-binding site of the antibody chains that harbors specificity for such target protein. There are three CDRs (CDR1-3, numbered sequentially from the N-terminus) in each human $V_L$ or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, international ImMunoGeneTics database (IMGT) (on the worldwide web at imgt.cines.fr/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Under Kabat, the CDR amino acid residues in the $V_H$ are numbered 31-35 (HCDR1), 50-65 (HCDR2), and 95-102 (HCDR3); and the CDR amino acid residues in the $V_L$ are numbered 24-34 (LCDR1), 50-56 (LCDR2), and 89-97 (LCDR3). Under Chothia, the CDR amino acids in the $V_H$ are numbered 26-32 (HCDR1), 52-56 (HCDR2), and 95-102 (HCDR3); and the amino acid residues in $V_L$ are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human $V_H$ and amino acid residues 24-34 (LCDR1), 50-56 (LCDR2), and 89-97 (LCDR3) in human $V_L$.

The term "binding specificity determinant" or "BSD" interchangeably refer to the minimum contiguous or non-contiguous amino acid sequence within a complementary determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity. For example, a mouse anti-TMEM16A antibody can be modified by replacing its constant region with the constant region from a human immunoglobulin. Due to the replacement with a human constant region, the chimeric antibody can retain its specificity in recognizing human TMEM16A while having reduced antigenicity in a human patient as compared to the original mouse antibody.

Antibodies or antigen-binding molecules of the invention further includes one or more immunoglobulin chains that are chemically linked to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (dAbs), and minibodies.

The various antibodies or antigen-binding fragments described herein can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources.

The term "variable region" or "V-region" interchangeably refer to a heavy or light chain comprising FR1-CDR1-FR2-CDR2-FR3-CDR3-FR4. An endogenous variable region is encoded by immunoglobulin heavy chain V-D-J genes or light chain V-J genes. A V-region can be naturally occurring, recombinant or synthetic.

As used herein, the term "variable segment" or "V-segment" interchangeably refer to a subsequence of the variable region including FR1-CDR1-FR2-CDR2-FR3. An endogenous V-segment is encoded by an immunoglobulin V-gene. A V-segment can be naturally occurring, recombinant or synthetic.

As used herein, the term "J-segment" refers to a subsequence of the variable region encoded comprising a C-terminal portion of a CDR3 and the FR4. An endogenous J-segment is encoded by an immunoglobulin J-gene. A J-segment can be naturally occurring, recombinant or synthetic.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *Proc. Natl. Acad. Sci. USA,* 81:6851-6855 (1984); Morrison and Oi, *Adv. Immunol.,* 44:65-92 (1988); Verhoeyen et al., *Science,* 239:1534-1536 (1988); Padlan, *Molec. Immun.,* 28:489-498 (1991); Padlan, *Molec. Immun.,* 31(3):169-217 (1994).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some complementary determining region ("CDR") residues and possibly some framework ("FR") residues are substituted by residues from analogous sites in rodent antibodies.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 94%, 96%, 98%, 99% sequence identity with the reference variable region nucleic acid or amino acid sequence. Corresponding human germline sequences can be determined, for example, through the publicly available international ImMunoGeneTics database (IMGT) (on the worldwide web at imgt.cines.frf) and V-base (on the worldwide web at vbase.mrc-cpe.cam.ac.uk).

The phrase "specifically (or selectively) bind," when used in the context of describing the interaction between an antigen, e.g., a protein, to an antibody or antibody-derived binding molecule, refers to a binding reaction that is determinative of the presence of the antigen in a heterogeneous population of proteins and other biologics, e.g., in a biological sample, e.g., a blood, serum, plasma or tissue sample. Thus, under designated immunoassay conditions, the antibodies or binding molecules with a particular binding specificity bind to a particular antigen at least two times the background and do not substantially bind in a significant amount to other antigens present in the sample. Specific binding to an antibody or binding molecule under such conditions may require the antibody or molecule to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^{-1}$, M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M $10^{-12}$ M or $10^{-13}$ M.

The term "epitope" refers to a site on an antigen to which a TMEM16A binding molecule of the invention specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "TMEM16A" refer to a calcium activated chloride channel belongs to the anoctamin/TEME16 family of membrane proteins. TMEM16 family has ten currently known members. TMEM16A and The term "TMEM16A" refer to a calcium activated chloride channel belongs to the anoctamin/TEME16 family of membrane proteins. TMEM16 family has ten currently known members. TMEM16A and TEMEM16B are the most homologous. TMEM16A pore forming region is highly conserved across the family. TMEM16A is expressed at high levels on certain cancer cells, such as gastrointestinal tract and head and neck cancers. The TMEM16A has four known splice variants named a, b, c. and d (see Table 1). Functional TMEM16A can be one of the following combinations of the splice variants: ac, abc, acd, or the abcd isoform. There is not a known isoform lacking all splice variants that is a functional chloride channel. The nucleic acid and amino acid sequences of human TMEM16A are known, and have been published in, e.g., Caputo A. et al., Science, 24:322(5901)590-594 (2008). One of the isoforms (the full length amino acid sequence) corresponds to NP_060513.5 plus a 22 amino acid in-frame insert variant b (ANO1-007 ENSP00000433445) from the Ensembl database (see the website at uswest.ensembl.org/index.html). TMEM16A sequences in some other species are also known. For example, mouse TMEM16A (NM_178642, NP_848757, Gene ID 101772) and rat TMEM16A (NM_001107564, NP_848757, Gene ID 309135) have been published. Structurally, a TMEM16A protein has eight transmembrane segments and cytosolic amino- and carboxy termini. TMEM16A also encompasses proteins that are a calcium activated chloride channel and have over its full length at least about 90%, 91%, 92%, 93%, 94%, 95%, 96%, 97%, 98%, 99% or 100% sequence identity with the amino acid sequence of SEQ ID NO:1 describe in Table 1 below. A TMEM16A nucleic acid sequence has over its full length at least about 90%, 91%, 92%, 93%, 94%, 95%, 96%, 97%, 98%, 99% or 100% sequence identity with the nucleic acid sequence of SEQ ID NO: 2 described in Table 1 below.

"Activity" of a protein of the invention refers to structural, regulatory, or biochemical functions of a protein in its native cell or tissue. Examples of activity of a polypeptide include both direct activities and indirect activities. Exemplary activities of TMEM16A include its role as a calcium activated chloride channel in normal epithelia cells, its robust overexpression in gastrointestinal stromal tumors, and its localization in the 11q13 amplicon present in esophagus squamous cell carcinomas. Therapeutically, antagonists of TMEM16A (e.g., antagonistic anti-TMEM16A antibodies) confer antitumor responses in vivo.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "cytotoxic agent" as used herein refers to a substance that inhibits or prevents the function of cells and/or causes destruction of cells. A cytotoxic agent can be, but not limited to, chemotherapeutic agents, toxins such as small molecule toxins or enzymatically active toxins of bacterial, fungal, plant or animal origin, including synthetic analogs and derivatives thereof, and radioactive isotopes (e.g. $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu).

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "link," when used in the context of describing how the antigen-binding portion are connected within a TMEM16A binding molecule of this invention, encompasses all possible means for physically joining the regions. A antigen-binding portion of a TMEM1A binding molecule of the invention and other portions of the molecule (e.g., a cytotoxic agent) are frequently joined by chemical bonds such as a covalent bond (e.g., a peptide bond or a disulfide bond) or a non-covalent bond, which can be either a direct bond (i.e., without a linker) or indirect bond (i.e., with the aid of at least one linker molecule between the antigen binding portion and the other portion, such as a cytotoxic agent).

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

The term "treat" and "treatment" refer to both therapeutic treatment and prophylactic or preventive measures, wherein the object is to prevent or slow down an undesired physiological change or disorder, such as the development or spread of cancer. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The term "therapeutically acceptable amount" or "therapeutically effective dose" interchangeably refer to an amount sufficient to effect the desired result (i.e., a reduction in tumor size, inhibition of tumor growth). In some embodiments, a therapeutically acceptable amount does not induce or cause undesirable side effects. A therapeutically acceptable amount can be determined by first administering a low dose, and then incrementally increasing that dose until the desired effect is achieved. A "therapeutically effective dosage" of a TMEM16A binding molecule of the invention can prevent the onset of, or result in a decrease in severity of, respectively, disease symptoms, including symptoms associated with cancer.

The term "co-administer" refers to the simultaneous presence of two active agents in the blood of an individual. Active agents that are co-administered can be concurrently or sequentially delivered.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than an anti-TMEM16A antibody (or fragments thereof, antibody drug conjugates thereof) of the invention. In some embodiments, the phrase "consisting essentially of" expressly excludes the inclusion of one or more additional active agents other than an anti-TMEM16A antibody (or fragments thereof, antibody drug conjugates thereof) of the invention and a second co-administered agent.

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for the preferential targeting of a pharmacological agent to the cancer cell. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal.

DETAILED DESCRIPTION

Figure 1:
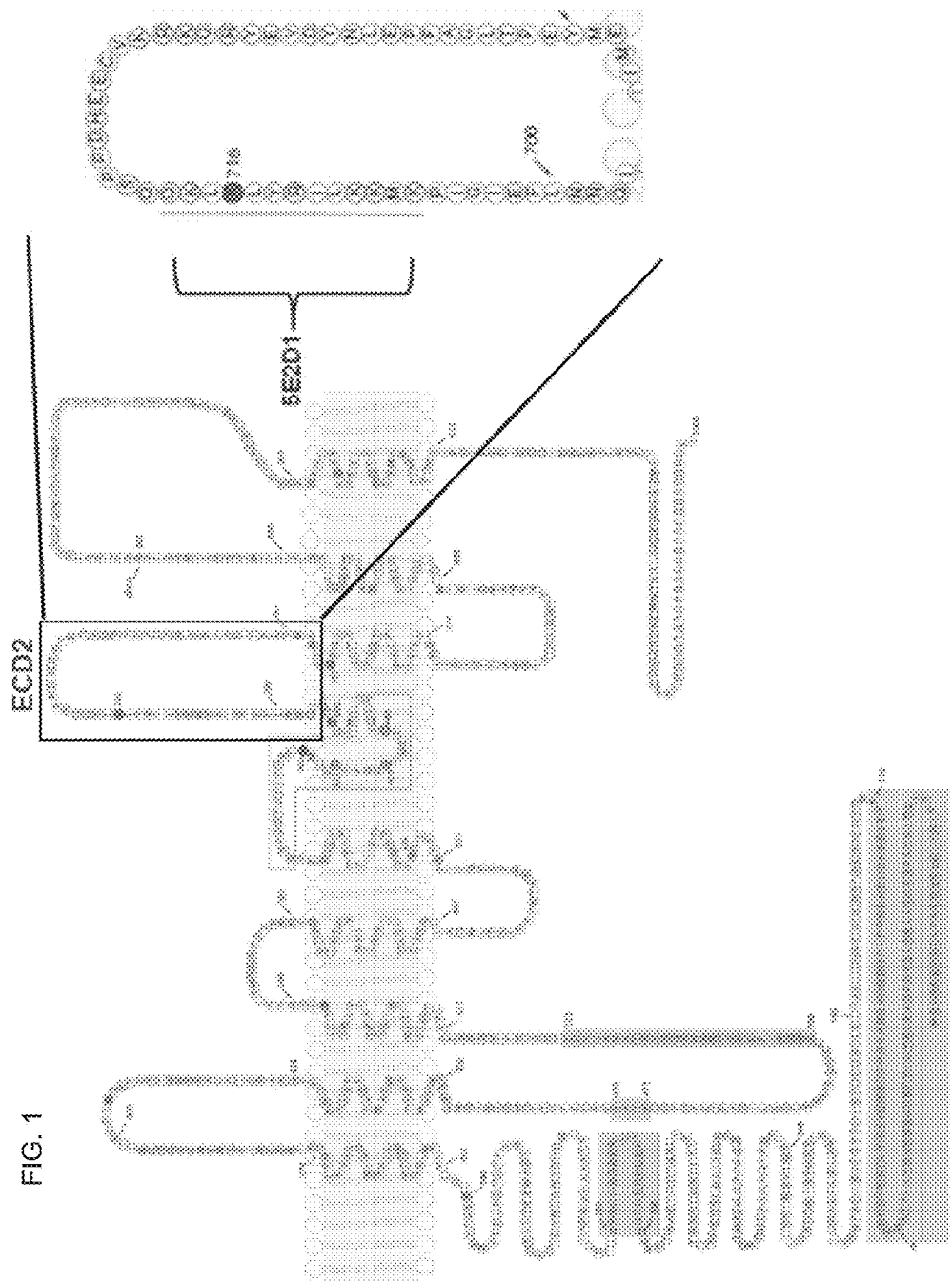
FIG. 1 shows human TMEM16A topology. Peptide sequence and localization of the TMEM16A antibody binding region on the ECD2 of TMEM16A (SEQ ID NO:1).

The present invention provides molecules that bind to TMEM16A ("TMEM16A binding molecules"), particularly human or humanized antibodies, antibody fragments, and antibody drug conjugates (ADCs) that bind to TMEM16A and modulate its functions. Epitopes of TMEM16A and molecules that bind to these epitopes are also provided herein. The TMEM16A binding molecules (e.g., antibodies, antibody fragments, and antibody drug conjugates) of the present invention find uses in diagnosis and treatment of cancer, e.g., gastrointestinal cancer, gastrointestinal stromal tumor, tumors of mesenchymal, epithelia, and stromal origin, esophageal squamous cell carcinoma, oral squamous cell carcinoma, cancers of the head and neck, and all other cancers containing the 11q13 amplification; as well as in diagnosis and treatment of other diseases, such as infections, inflammatory or immunological diseases.

The full length sequence of human TMEM16A is described in Caputo A. et al., Science, 24:322(5901)590-594 (2008), and is shown in Table 1 as SEQ ID NO: 1 (amino acid sequence) and SEQ ID NO:2 (nucleic acid sequence). This is the full length aa sequence corresponding to NP_060513.5 plus a 22 amino acid in-frame insert variant b [ANO1-007 ENSP00000433445] from the Ensembl database (see, us-west.ensembl.org/index.html).

TABLE 1

Human TMEM16A Amino Acid and Nucleic Acid Sequences

Amino acid sequence of human TMEM16A(abcd) (SEQ ID NO: 1, 1008 amino acids).
MRVNEKYSTLPAEDRSVHIINICAIEDIGYLPSEGTLLNSLSVDPDAECKYGLYFRDGRRKVDYILVYHHKRPSGNRTL
VRRVQHSDTPSGARSVKQDHPLPGKGASLDAGSGEPPMDYHEDDKRFRREEYEGNLLEAGLELERDEDTKIHGVGFVKI
HAPWNVLCREAEFLKLKMPTKKMYHINETRGLLKKINSVLQKITDPIQPKVAEHRPQTMKRLSYPFSREKQHLFDLSDK
DSFFDSKTRSTIVYEILKRTTCTKAKYSMGQGEGRKKDSALLSKRRKCGKYGITSLLANGVYAAAYPLHDGDYNGENVE
FNDRKLLYEEWARYGVFYKYQPIDLVRKYFGEKIGLYFAWLGVYTQMLIPASIVGIIVFLYGCATMDENIPSMEMCDQR
HNITMCPLCDKTCSYWKMSSACATARASHLFDNPATVFFSVFMALWAATFMEHWKRKQMRLNYRWDLTGFEEEEEAVKD
HPRAEYEARVLEKSLKKESRNKEKRRHIPEESTNKWKQRVKTAMAGVKLTDKVKLTWRDRFPAYLTNLVSIIFMIAVTF
AIVLGVIIYRISMAAALAMNSSPSVRSNIRVTVTATAVIINLVVIILLDEVYGCIARWLTKIEVPKTEKSFEERLIFKA
FLLKFVNSYTPIFYVAFFKGRFVGRPGDYVYIFRSFRMEECAPGGCLMELCIQLSIIMLGKQLIQNNLFEIGIPKMKKL
IRYLKLKQQSPPDHEECVKRKQRYEVDYNLEPFAGLTPEYMEMIIQFGFVTLFVASFPLAPLFALLNNIIEIRLDAKKF
VTELRRPVAVRAKDIGIWYNILRGIGKLAVIINAFVISFTSDFIPRLVYLYMYSKNGTMHGFVNHTLSSFNVSDFQNGT
APNDPLDLGYEVQICRYKDYREPPWSENKYDISKDFWAVLAARLAFVIVFQNLVMFMSDFVDWVIPDIPKDISQQIHKE
KVLMVELFMREEQDKQQLLETWMEKERQKDEPPCNHHNTKACPDSLGSPAPSHAYHGGVL Nucleic Acid Sequence of human TMEM16A (SEQ ID NO: 2)
```
   1 aaaggcgggc cggctggcgt ccaagttcct gaccaggcgc gggccggccc gcggaccag
  61 cagccgggtg gcggcgcgat cggccccgag aggctcaggc gccccgca tcgagcgcgc
 121 gggccgggcg gccagggcg gcgggcggag cgggaggcgg ccacgtcccc ggcgggcctg
 181 ggcgcgggga ggcccggccc cctgcgagcg cgccgcgaac gctgcggtct ccgcccgcag
 241 aggccgccgg ggccgtggat ggggagggcg cgccgcccgg cggtcccagc gcacaggcgg
 301 ccacgatgag ggtcaacgag aagtactcga cgctcccggc cgaggaccgc agcgtccaca
 361 tcatcaacat ctgcgccatc gaggacatcg gctacctgcc gtccgagggc acgctgctga
 421 actccttatc tgtggaccct gatgccgagt gcaagtatgg cctgtacttc agggacggcc
 481 ggcgcaaggt ggactacatc ctggtgtacc atcacaagag gccctcgggc aaccggaccc
 541 tggtcaggag ggtgcagcac agcgacaccc cctctgggc tcgcagcgtc aagcaggacc
 601 accccctgcc gggcaagggg gcgtcgctgg atgcaggctc ggggagccc ccgatggact
 661 accacgagga tgacaagcgc ttccgcaggg aggagtacga gggcaacctc ctggaggcgg
 721 gcctggagct ggagcgggac gaggacacta aaatccacgg agtcgggttt gtgaaaatcc
 781 atgccccctg gaacgtgctg tgcagagagg ccgagttcct gaaactgaag atgccgacga
 841 agaagatgta ccacattaat gagacccgtg gcctcctgaa aaaatcaac tctgtgctcc
 901 agaaaatcac agatcccatc cagcccaaag tggctgagca caggcccag accatgaaga
 961 gactctccta tccttctcc cgggagaagc agcatctatt tgacttgtct gataaggatt
1021 ccttttttcga cagcaaaacc cggagcacga ttgtctatga gatcttgaag agaacgacgt
1081 gtacaaaggc caagtacagc atgggccaag gcgagggaag aaagaaggac tccgccttc
1141 taagtaaaag gcggaaatgt gggaagtatg catcacgag cctgctggcc aatggtgtgt
1201 acgcggctgc atacccactg cacgatggag actacaacgg tgaaaacgtc gagttcaacg
1261 acagaaaact cctgtacgaa gagtgggcac gctatggagt tttctataag taccagccca
1321 tcgacctggt caggaagtat tttggggaga gatcggcct gtacttcgcc tggctgggcg
1381 tgtacaccca tgatgctcatc cctgcctcca tcgtgggaat cattgtcttc ctgtacggat
1441 gcgccaccat ggatgaaaac atccccagca tggagatgtg tgaccagaga cacaatatca
```

TABLE 1-continued

Human TMEM16A Amino Acid and Nucleic Acid Sequences

```
1501 ccatgtgccc gctttgcgac aagacctgca gctactggaa gatgagctca gcctgcgcca
1561 cggcccgcgc cagccacctc ttcgacaacc ccgccacggt cttcttctct gtcttcatgg
1621 ccctctgggc tgccaccttc atggagcact ggaagcggaa acagatgcga ctcaactacc
1681 gctgggacct cacgggcttt gaagaggaag aggaggctgt caaggatcat cctagagctg
1741 aatacgaagc cagagtcttg gagaagtctc tgaagaaaga gtccagaaac aaagagaagc
1801 gccggcatat tccagaggag tcaacaaaca aatggaagca gagggttaag acagccatgg
1861 cgggggtgaa attgactgac aaagtgaagc tgacatggag agatcggttc ccagcctacc
1921 tcactaactt ggtctccatc atcttcatga ttgcagtgac gtttgccatc gtcctcggcg
1981 tcatcatcta cagaatctcc atggccgccg ccttggccat gaactcctcc cctccgtgc
2041 ggtccaacat ccgggtcaca gtcacagcca ccgcagtcat catcaaccta gtggtcatca
2101 tcctcctgga cgaggtgtat ggctgcatag cccgatggct caccaagatc gaggtcccaa
2161 agacggagaa aagctttgag gagaggctga tcttcaaggc tttcctgctg aagtttgtga
2221 attcctacac ccccatcttt tacgtggcgt tcttcaaagg ccggtttgtt ggacgcccgg
2281 gcgactacgt gtacattttc cgttccttcc gaatggaaga gtgtgcgcca ggggctgcc
2341 tgatggagct atgcatccag ctcagcatca tcatgctggg gaaacagctg atccagaaca
2401 acctgttcga gatcggcatc ccgaagatga agaagctcat ccgctacctg aagctgaagc
2461 agcagagccc ccctgaccac gaggagtgtg tgaagaggaa acagcggtac gaggtggatt
2521 acaacctgga gcccttcgcg ggcctcaccc cagagtacat ggaaatgatc atccagtttg
2581 gcttcgtcac cctgtttgtc gcctccttcc ccctggcccc actgtttgcg ctgctgaaca
2641 acatcatcga gatccgcctg gacgccaaaa agtttgtcac tgagctccga aggccggtag
2701 ctgtcagagc caaagacatc ggaatctggt acaatatcct cagaggcatt gggaagcttg
2761 ctgtcatcat caatgccttc gtgatctcct tcacgtctga cttcatcccg cgcctggtgt
2821 acctctacat gtacagtaag aacgggacca tgcacggctt cgtcaaccac accctctcct
2881 ccttcaacgt cagtgacttc cagaacggca cggcccccaa tgacccctg gacctgggct
2941 acgaggtgca gatctgcagg tataaagact accgagagcc gccgtggtcg gaaaacaagt
3001 acgacatctc caaggacttc tgggccgtcc tggcagcccg gctggcgttt gtcatcgtct
3061 tccagaacct ggtcatgttc atgagcgact tgtggactg ggtcatcccg gacatcccca
3121 aggacatcag ccagcagatc cacaaggaga aggtgctcat ggtggagctg ttcatgcggg
3181 aggagcaaga caagcagcag ctgctggaaa cctggatgga aaggagcgg cagaaggacg
3241 agccgccgtg caaccaccac aacaccaaag cctgcccaga cagcctcggc agcccagccc
3301 ccagccatgc ctaccacggg ggcgtcctgt agctatgcca gcgggctgg gcaggccagc
3361 cgggcatcct gaccgatggg caccctctcc cagggcaggc ggcttccgc tccaccagg
3421 gcccggtggg tcctgggttt tctgcaaaca tggaggacca ctttctgata ggacattttc
3481 ctttcttctt tctgtttct ttcccttgtt tttgcacaaa gccattatgc agggaatatt
3541 ttttaatctg tagtattcaa gatgaatcaa aatgatggct ggtaatacgg caataaggta
3601 gcaaaggcag gtgctttgca gaaagaatgc ttggaaactt gagtctccct agaggtgaaa
3661 agtgagcaga ggcccgtaga aaccctcctc tgaatcctcc taattcctta agatagatgc
3721 aaaatggtaa gccgaggcat cgcgcaaaag ctggtgcgat gcttcaggga aaatggaaaa
3781 cccacgcaag aataatgatt gattccggtt ccaaaaggtg tcacctacct gtttcagaaa
```

TABLE 1-continued

Human TMEM16A Amino Acid and Nucleic Acid Sequences

```
3841 agttagactt tccatcgcct tttccttcca tcagttgagt ggctgagaga gaagtgcctc 3901 atccctgagc cacacagggg gcgtgggagc atcccagtta tccctggaaa gctagaaggg 3961 gacagaggtg tccctgatta agcaggaaac agcacccttg gcgtccccag caggctcccc 4021 actgtcagcc acacacctgc ccccatcaca ccaagccgac ctcagagttg ttcatcttcc 4081 ttatgggaca aaaccggttg accagaaaat gggcagagag agatgacctg gaagcatttc 4141 cacagatggt gtcagggttt caagaagtct tagggcttcc aggggtcccc tggaagcttt 4201 agaatattta tgggtttttt tttcaaatat caattatatg gtagattgag gattttttt 4261 ctgtagctca aaggtggagg gagtttatta gttaaccaaa tatcgttgag aggaatttaa 4321 aatactgtta ctaccaaaga tttttattaa taaaggctta tattttggta acacttctct 4381 atatttttac tcacaggaat gtcactgttg gacaattatt ttaaaagtgt ataaaaccaa 4441 gtctcataaa tgatatgagt gatctaaatt tgcagcaatg atactaaaca actctctgaa 4501 atttctcaag caccaagaga aacatcattt tagcaaaggc caggaggaaa aatagaaata 4561 aatttgtctt gaagatctca ttgatgtgat gttacattcc ctttaatctg ccaactgtgg 4621 tcaaagttca taggtgtcgt acatttccat tatttgctaa aatcatgcaa tctgatgctt 4681 ctcttttctc ttgtacagta agtagtttga agtgggtttt gtatataaat actgtattaa 4741 aaattaggca attaccaaaa atccttttat ggaaaccatt tttttaaaaa gtgaatgtac 4801 acaaatccac agaggactgt ggctggacat tcatctaaat aaatttgaat atacgacact 4861 tttctcactt gaaaaa
```

The TMEM16A has four known splice variants named a, b, c. and d. Functional TMEM16A can be one of the following combinations of the splice variants: ac, abc, acd, or the abcd isoform. The sequences corresponding to the four splice variants a, b, c, and d are highlighted in bold and underlined in Table 1. The position of the four segments is the following: (a) amino acids 1-116; (b) amino acids 268-289; (c) amino acids 470-473; and (d) amino acids 498-523. These four segments are predicted to be exposed to the cytosol. The open reading frame of the gene is defined by position 306-3332 of SEQ ID NO:2 in Table 1, which encodes a 1008 long amino acid sequence (TMEM16A with all four splice variants abcd).

The present invention is based, in part, on the discovery that certain antibodies or antigen binding fragments thereof are capable of internalization upon binding to the ECD2 domain of TMEM16A. Accordingly, the present invention provides molecules, particularly human or humanized antibodies, antibody fragments, and antibody drug conjugates, that bind to human TMEM16A extracellular domain 2 (ECD2) and internalize into the cell upon such binding. In some embodiments, the present invention provides molecules, particularly human or humanized antibodies, antibody fragments, and antibody drug conjugates, that specifically bind to (1) a peptide comprising or consisting of amino acid sequence that is at least 60%, at least 70%, at least 80%, at least 90%, or 100% identical to KLIRYLKLKQ (SEQ ID NO:3); and (2) ECD2 of human TMEM16A. ECD2 as the binding site has several advantages, for example, there is only one cysteine with unknown bridging pattern to other loop and no potential glycosylation site; ECD2 is also in proximity to the active site of the channel and antigen binding molecules binding to this region are likely to disrupt and/or block the channel function; and finally, this region is least similar to other TMEM16 family members and not likely to cross react.

The TMEM16A binding antibodies (and fragments thereof) of the invention can internalize and thus ideal candidates for using as antibody drug conjugates (e.g., link to a cytotoxic agent or other type of payload) to treat cancer. Such benefits as well as other benefits of the antigen binding molecules of the invention are demonstrated throughout the specification.

1. Anti-TMEM16A Antibodies

Accordingly, the present invention provides TMEM16A binding antibodies, antibody fragments, and antibody drug conjugates that can be used for treating cancer, infections, and inflammatory or immunological diseases. In some embodiments, the TMEM16A binding antibodies (or fragments thereof) of the invention are non-human antibodies, e.g., mouse antibodies (or fragments thereof). In some embodiments, the TMEM16A binding antibodies (or antigen binding fragments thereof) of the invention are human or humanized antibodies (or fragments thereof). In some embodiments, the antibodies (or antigen binding fragments thereof) of the invention can bind to TMEM16A and inhibit one or more of its activities (antagonist antibody). In some embodiments, the antibodies (or fragments thereof) of the invention can bind to TMEM16A and enhance one or more of its activities (agonist antibody). In some embodiments, the antibodies (or antigen binding fragments thereof) of the invention are capable of binding to TMEM16A, but do not affect its activities. Both types of antibodies can be used in the antibody drug conjugates context.

In one embodiment, the present invention provides an antibody (or antigen binding fragment thereof) that specifically binds to ECD2 of TMEM16A and internalize upon such binding. In another embodiment, the present invention provides an antibody (or antigen binding fragment thereof) that specifically binds to (1) a peptide comprising or consisting of an amino acid sequence that is at least 60%, at least 70%, at least 80%, at least 90%, or 100% identical to KLIRYKLKLQ (SEQ ID NO: 3); and (2) ECD2 of human TMEM16A.

In one embodiment, the present invention provides an antibody (or an antigen binding fragment thereof) that specifically binds to an epitope of human TMEM16A comprising or consisting of an amino acid sequence that is at least 60%, at least 70%, at least 80%, at least 90%, or 100% identical to KLIRYKLKLQ (SEQ ID NO: 3), or a portion thereof. In some embodiments, the antibodies of the invention (or antigen binding fragments thereof) specifically bind to an epitope on ECD2 of TMEM16A that comprises or consisting of an amino acid sequence that is at least 60%, at least 70%, at least 80%, at least 90%, or 100% identical to KLIRYKLKLQ (SEQ ID NO: 3), or a portion thereof. In some embodiments, such antibodies (or antigen binding fragments thereof) are human antibodies. In some embodiments, such antibodies (or antigen binding fragments thereof) are humanized antibodies.

In some embodiments, the antibodies (or antigen binding fragments thereof) internalize into a cell upon binding to TMEM16A, and thus are good candidates for antibody drug conjugates (ADCs).

In one embodiment, the present invention provides a mouse antibody, or an antigen biding fragment thereof, that bind to TMEM16A ECD2, and generated by using KLIRYKLKLQ (SEQ ID NO: 3) peptide as the antigen. In another embodiment, the present invention provides a humanized version of the mouse antibody (or antigen binding fragment thereof).

In some embodiments, the anti-TMEM16A antibodies contain a minimum binding sequence determinant (BSD) within the CDR3 of the heavy and light chains derived from the originating or reference monoclonal antibody (e.g., the mouse antibody described above). The remaining sequences of the heavy chain and light chain variable regions (CDR and FR), e.g., V-segment and J-segment, are from corresponding human germline and affinity matured amino acid sequences. The V-segments can be selected from a human V-segment library. Further sequence refinement can be accomplished by affinity maturation.

In another embodiment, the heavy and light chains of the anti-TMEM16A antibodies contain a human V-segment from the corresponding human germline sequence (FR1-CDR1-FR2-CDR2-FR3), e.g., selected from a human V-segment library, and a CDR3-FR4 sequence segment from the originating monoclonal antibody. The CDR3-FR4 sequence segment can be further refined by replacing sequence segments with corresponding human germline sequences and/or by affinity maturation. For example, the FR4 and/or the CDR3 sequence surrounding the BSD can be replaced with the corresponding human germline sequence, while the BSD from the CDR3 of the originating monoclonal antibody is retained.

The present invention provides fully human antibodies that specifically bind to a TMEM16A protein (e.g., human TMEM16A). Compared to the chimeric or humanized antibodies, the human TMEM16A-binding antibodies of the invention have further reduced antigenicity when administered to human subjects.

The human TMEM16A-binding antibodies can be generated using methods that are known in the art. For example, the Humaneering™ technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody.

The anti-TMEM16A antibodies of the invention are based on engineered human antibodies with V-region sequences having substantial amino acid sequence identity to human germline V region sequences while retaining the specificity and affinity of a reference antibody. See, U.S. Patent Publication No. 2005/0255552 and U.S. Patent Publication No. 2006/0134098, both of which are hereby incorporated herein by reference. The process of improvement identifies minimal sequence information required to determine antigen-binding specificity from the variable region of a reference antibody, and transfers that information to a library of human partial V-region gene sequences to generate an epitope-focused library of human antibody V regions. A microbial-based secretion system can be used to express members of the library as antibody Fab fragments and the library is screened for antigen-binding Fabs, for example, using a colony-lift binding assay. See, e.g., U.S. Patent Publication No. 2007/0020685. Positive clones can be further characterized to identify those with the highest affinity. The resultant engineered human Fabs retain the binding specificity of the parent, reference anti-TMEM16A antibody, typically have equivalent or higher affinity for antigen in comparison to the parent antibody, and have V-regions with a high degree of sequence identity compared with human germ-line antibody V-regions.

The minimum binding specificity determinant (BSD) required to generate the epitope-focused library is typically represented by a sequence within the heavy chain CDR3 ("CDRH3") and a sequence within the light chain of CDR3 ("CDRL3"). The BSD can comprise a portion or the entire length of a CDR3. The BSD can be comprised of contiguous or non-contiguous amino acid residues. In some cases, the epitope-focused library is constructed from human V-segment sequences linked to the unique CDR3-FR4 region from the reference antibody containing the BSD and human germline J segment sequences (see, U.S. Patent Publication No. 2005/0255552). Alternatively, the human V segment libraries can be generated by sequential cassette replacement in which only part of the reference antibody V segment is initially replaced by a library of human sequences. The identified human "cassettes" supporting binding in the context of residual reference antibody amino acid sequences are then recombined in a second library screen to generate completely human V segments (see, U.S. Patent Publication No. 2006/0134098).

In each case, paired heavy and light chain CDR3 segments, CDR3-FR4 segments, or J segments, containing specificity determinants from the reference antibody, are used to constrain the binding specificity so that antigen-binders obtained from the library retain the epitope-specificity of the reference antibody. Additional maturational changes can be introduced in the CDR3 regions of each chain during the library construction in order to identify antibodies with optimal binding kinetics. The resulting engineered human antibodies have V-segment sequences derived from the human germ-line libraries, retain the short BSD sequence from within the CDR3 regions and have human germ-line framework 4 (FR4) regions.

The anti-TMEM16A antibodies of the present invention generally will bind TMEM16A with an equilibrium dissociation constant ($K_D$) of less than about $10^{-8}$ M or $10^{-9}$ M, for example, less than about $10^{-10}$ M or $10^{-11}$ M, in some embodiments less than about $10^{-12}$ M or $10^{-13}$ M.

The anti-TMEM16A antibodies optionally can be multimerized and used according to the methods of this invention. The anti-TMEM16A antibodies can be a full-length tetrameric antibody (i.e., having two light chains and two heavy chains), a single chain antibody (e.g., a scFv), or a molecule comprising antibody fragments that form one or more antigen-binding sites and confer TMEM16A-binding specificity, e.g., comprising heavy and light chain variable regions (for instance, Fab' or other similar fragments).

Antibodies that Bind to the Same Epitope

The present invention provides antibodies that bind to an epitope region comprising or consisting of KLIRYLKLKQ (SEQ ID NO:3), amino acids 707-719 of ECD2 of TMEM16A, or a portion thereof. The present invention also provides antibodies that bind to the same epitope as does the TMEM16A-binding antibody 5E2D1 (or a humanized version thereof). Additional antibodies can therefore be identified based on their ability to cross-compete (e.g., to competitively inhibit the binding of, in a statistically significant manner) with 5E2D1 (or a humanized version thereof) in TMEM16A binding assays. Competitive inhibition can occur, for example, if the TMEM16A binding molecules bind to identical or structurally similar epitopes (e.g., overlapping epitopes), or spatially proximal epitopes which, when bound, causes steric hindrance between the antibodies. The ability of a test antibody to inhibit the binding of 5E2D1 (or a humanized version thereof) to a TMEM16A protein demonstrates that the test antibody can compete with 5E2D1 (or a humanized version thereof) for binding to TMEM16A; such an antibody may, according to non-limiting theory, bind to the same or a related (e.g., a structurally similar or spatially proximal) epitope on the TMEM16A protein as the antibody with which it competes. In a certain embodiment, the antibody that binds to the same epitope on TMEM16A as the antibodies of the present invention is a human or humanized monoclonal antibody. Such human or humanized monoclonal antibodies can be prepared and isolated as described herein and methods well known in the art.

Competitive inhibition can be determined using routine assays in which the TMEM16A binding molecule under test inhibits specific binding of a reference TMEM16A binding molecule to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)). Typically, such an assay involves the use of purified antigen bound to a solid surface or cells bearing either of these, an unlabeled test TMEM16A binding molecule and a labeled reference TMEM16A binding molecule. Competitive inhibition is measured by determining the amount of label bound to the solid surface or cells in the presence of the test TMEM16A binding molecule. Usually the test TMEM16A binding molecule is present in excess. Usually, when a competing TMEM16A binding molecule is present in excess, it will inhibit specific binding of a reference TMEM16A binding molecule to a common antigen by at least 50-55%, 55-60%, 60-65%, 65-70% 70-75% or more.

Other techniques include, for example, epitope mapping methods, such as, x-ray analyses of crystals of antigen: TMEM16A binding molecule complexes which provides atomic resolution of the epitope. Other methods monitor the binding of the TMEM16A binding molecule to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the TMEM16A binding molecule of interest to affinity isolate specific short peptides from combinatorial phage display peptide libraries. The peptides are then regarded as leads for the definition of the epitope corresponding to the TMEM16A binding molecule used to screen the peptide library. For epitope mapping, computational algorithms have also been developed which have been shown to map conformational discontinuous epitopes.

Engineered and Modified Antibodies

An antibody of the invention further can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of a specific antibody by constructing expression vectors that include CDR sequences from the specific antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or an antigen binding fragment thereof, that binds to ECD2, or an epitope region comprising or consisting of KLIRYLKLKQ (SEQ ID NO:3), or a portion thereof such antibodies contain the $V_H$ and $V_L$ CDR sequences of monoclonal antibodies from one species (e.g., mouse), yet may contain different framework sequences from another species (e.g., human).

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J. Immunol. 24:827-836.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications can be introduced. The mutations may be amino acid substitutions, additions or deletions. Moreover, typically no more than one, two, three, four or five residues within a CDR region are altered.

Framework or Fc Engineering

When present, the constant regions of the anti-TMEM16A antibodies can be any type or subtype, as appropriate, and can be selected to be from the species of the subject to be treated by the present methods (e.g., human, non-human primate or other mammal, for example, agricultural mammal (e.g., equine, ovine, bovine, porcine, camelid), domestic mammal (e.g., canine, feline) or rodent (e.g., rat, mouse, hamster, rabbit). In some embodiments the anti-TMEM16A antibodies are humanized or Humaneered™. In some embodiments, the constant region isotype is IgG, for example, IgG1.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor (FcR) or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

Antibodies containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to Ala234 and Ala235.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to TMEM16A. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target TMEM16A protein (e.g., human TMEM16A). Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for TMEM16A. In certain embodiments herein, the camelid antibody or nanobody is naturally produced in the camelid animal, i.e., is produced by the camelid following immunization with TMEM16A or a peptide fragment thereof, using techniques described herein for other antibodies. Alternatively, the TMEM16A-binding camelid nanobody is engineered, i.e., produced by selection for example from a library of phage displaying appropriately mutagenized camelid nanobody proteins using panning procedures with TMEM16A as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising an TMEM16A-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for TMEM16A and a second binding specificity for a second target epitope. For example, the second target epitope is another epitope of TMEM16A different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which $V_H$ and $V_L$ domains are expressed on a single polypeptide chain, connected by a linker that is too short to allow for pairing between the two domains on the same chain. The $V_H$ and $V_L$ domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA ($V_H$-$V_L$ configuration), or VLA-VHB and VLB-VHA ($V_L$-$V_H$ configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4): 128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4): 2856-65).

Other antibodies which can be employed in the bispecific molecules of the invention are murine, chimeric and humanized monoclonal antibodies.

The bispecific molecules of the present invention can be prepared by linking the constituent binding specificities, using methods known in the art. For example, each binding specificity of the bispecific molecule can be generated separately and then linked to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be linked by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013, 653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent molecules comprising at least two identical or different antigen binding portions of the antibodies of the invention, where such molecules may be dimers, trimers, tetramers, or higher order multimers and may be homomeric or heteromeric, that is, they may comprise multiple polypeptide chains that are the same or different. The antigen-binding portions can be linked together via protein fusion or covalent or non covalent linkage. Alternatively, methods of linkage have been described for the bispecfic molecules. Tetravalent molecules can be obtained for example by cross-linking antibodies of the antibodies of the invention with an antibody that binds to the constant regions of the antibodies of the invention, for example the Fc or hinge region. Trimerizing domain are described for example in Borean patent EP 1 012 280B1. Pentamerizing modules are described for example in PCT/EP97/05897.

In one embodiment, multispecific binding domain proteins are produced by linking an scFv to an IgG antibody. The $V_H$ and $V_L$ domains used to make an scFv may be derived from the same or from different antibodies. The scFv comprises at least one, two, three, four, five, or six CDRs. The multispecific epitope binding proteins of the invention comprise one, two, three, four, or more polypeptide chains. The epitope binding domains may also be scFvs, single chain diabodies, variable regions of antibodies (e.g., heavy chain and/or light chain variable regions), IgG antibodies, or peptidomimetics.

Antibodies with Extended Half Life

The present invention provides for antibodies that specifically bind to TMEM16A protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanoboies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in *E. coli*, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defence system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The strategies for increasing half life is especially useful in nanobodies, fibronectin-based binders, and other antibodies or proteins for which increased in vivo half life is desired.

2. Antibody Conjugates

The present invention further encompasses uses of TMEM16A antibodies or fragments thereof linked to a therapeutic moiety. An antibody or fragment thereof may be linked to a therapeutic moiety such as a cytotoxic agent or an anti-cancer agent. The conjugate may consist of a liable or non-liable linker made up of any composition of synthetic chemistry or peptide that is condusive to generation of a stable antibody linker.

Further, an antibody or fragment thereof may be linked to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be linked to therapeutic moieties such as a radioactive metal ion, such as alph-emiters such as 213Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

The present invention also provides antibodies or fragments thereof that specifically bind to a TMEM16A protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a $V_H$ domain, a $V_H$ CDR, a $V_L$ domain or a $V_L$ CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a TMEM16A protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof linked to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149 Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

3. Methods of Producing Antibodies of the Invention

Once an archetypal anti-human TMEM16A antibody, for example, 5E2D1, has been isolated that has the desired properties (e.g., internalizing upon binding) described herein, it is straightforward to generate other antibodies with similar properties, using art-known methods (see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., supra; Marks et al., *Biotechnology*, 10:779-783, (1992)).

Nucleic Acid Molecules Encoding Antibodies of the Invention

Another aspect of the invention pertains to nucleic acid molecules that encode the TMEM16A binding molecules of the invention. The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554).

Monoclonal Antibody Generation

Monoclonal antibodies (mAbs) can be produced by a variety of techniques, including conventional monoclonal antibody methodology e.g., the standard somatic cell hybridization technique of Kohler and Milstein (1975 Nature, 256: 495), or using library display methods, such as phage display.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539, and U.S. Pat. Nos. 5,530,101; 5,585,089; 5,693,762 and 6,180,370.

In a certain embodiment, the antibodies of the invention are human monoclonal antibodies. Such human monoclonal antibodies directed against TMEM16A can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb mouse (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see, e.g., Lonberg et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y.

Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Pub. Nos. WO 92103918, WO 93/12227, WO 94/25585, WO 97113852, WO 98/24884 and WO 99/45962, all to Lonberg and Kay; and PCT Pub. No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in WO 02/43478.

Still further, alternative transgenic animal systems expressing human immunoglobulin genes are available in the art and can be used to raise anti-TMEM16A antibodies of the invention. For example, an alternative transgenic system referred to as the Xenomouse® (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-TMEM16A antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-TMEM16A antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Libraries can be screened for binding to full length TMEM16A or to a particular epitope of TMEM16A (e.g., KLIRYKLKLQ).

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Human Monoclonal Antibodies in Human Ig Mice

Purified recombinant human TMEM16A expressed in prokaryotic cells (e.g., *E. coli*) or eukaryotic cells (e.g., mammalian cells, e.g., HEK293 cells) can be used as the antigen. The protein can be linked to a carrier, such as keyhole limpet hemocyanin (KLH).

Fully human monoclonal antibodies to TMEM16A are prepared using HCo7, HCo12 and HCo17 strains of HuMab transgenic mice and the KM strain of transgenic transchromosomic mice, each of which express human antibody genes. In each of these mouse strains, the endogenous mouse kappa light chain gene can be homozygously disrupted as described in Chen et al., 1993 EMBO J. 12:811-820 and the endogenous mouse heavy chain gene can be homozygously disrupted as described in Example 1 of WO 01109187. Each of these mouse strains carries a human kappa light chain transgene, KCo5, as described in Fishwild et al., 1996 Nature Biotechnology 14:845-851. The HCo7 strain carries the HCo7 human heavy chain transgene as described in U.S. Pat. Nos. 5,545, 806; 5,625,825; and 5,545,807. The HCo12 strain carries the HCo12 human heavy chain transgene as described in Example 2 of WO 01/09187. The HCo17 stain carries the HCo17 human heavy chain transgene. The KNM strain contains the SC20 transchromosome as described in WO 02/43478.

To generate fully human monoclonal antibodies to TMEM16A, HuMab mice and KM mice are immunized with purified recombinant TMEM16A, a TMEM16A fragment (e.g., a peptide comprising or consisting of SEQ ID NO:3), or a conjugate thereof (e.g., TMEM16A-KLH) as antigen. General immunization schemes for HuMab mice are described in Lonberg, N. et al., 1994 Nature 368(6474): 856-859; Fishwild, D. et al., 1996 Nature Biotechnology 14:845-851 and WO 98/24884. The mice are 6-16 weeks of age upon the first infusion of antigen. A purified recombinant preparation (5-50 µg) of the antigen is used to immunize the HuMab mice and KM mice in the peritoneal cavity, subcutaneously (Sc) or by footpad injection.

Transgenic mice are immunized twice with antigen in complete Freund's adjuvant or Ribi adjuvant either in the peritoneal cavity (IP), subcutaneously (Sc) or by footpad (FP), followed by 3-21 days IP, Sc or FP immunization (up to a total of 11 immunizations) with the antigen in incomplete Freund's or Ribi adjuvant. The immune response is monitored by retroorbital bleeds. The plasma is screened by ELISA, and mice with sufficient titers of anti-TMEM16A human immunogolobulin are used for fusions. Mice are boosted intravenously with antigen 3 and 2 days before sacrifice and removal of the spleen. Typically, 10-35 fusions for each antigen are performed. Several dozen mice are immunized for each antigen. A total of 82 mice of the HCo7, HCo12, HCo17 and KM mice strains are immunized with TMEM16A.

To select HuMab or KM mice producing antibodies that bound TMEM16A, sera from immunized mice can be tested by ELISA as described by Fishwild, D. et al., 1996. Briefly, microtiter plates are coated with purified recombinant TMEM16A at 1-2 µg/ml in PBS, 50 µl/wells incubated 4° C. overnight then blocked with 200 µg/well of 5% chicken serum in PBS/Tween (0.05%). Dilutions of plasma from TMEM16A-immunized mice are added to each well and incubated for 1-2 hours at ambient temperature. The plates are washed with PBS/Tween and then incubated with a goat-anti-human IgG Fc polyclonal antibody conjugated with horseradish peroxidase (HRP) for 1 hour at room temperature. After washing, the plates are developed with ABTS substrate (Sigma, A-1888, 0.22 mg/ml) and analyzed by spectrophotometer at OD 415-495. Splenocytes of mice that developed the highest titers of anti-TMEM16A antibodies are used for fusions. Fusions are performed and hybridoma supernatants are tested for anti-TMEM16A activity by ELISA.

The mouse splenocytes, isolated from the HuMab mice and KM mice, are fused with PEG to a mouse myeloma cell line based upon standard protocols. The resulting hybridomas are then screened for the production of antigen-specific antibodies. Single cell suspensions of splenic lymphocytes from immunized mice are fused to one-fourth the number of SP2/0 nonsecreting mouse myeloma cells (ATCC, CRL 1581) with 50% PEG (Sigma). Cells are plated at approximately $1 \times 10^5$/ well in flat bottom microtiter plates, followed by about two weeks of incubation in selective medium containing 10% fetal bovine serum, 10% P388D 1 (ATCC, CRL TIB-63) conditioned medium, 3-5% Origen® (IGEN) in DMEM (Mediatech, CRL 10013, with high glucose, L-glutamine and sodium pyruvate) plus 5 mM HEPES, 0.055 mM 2-mercaptoethanol, 50 μg/ml gentamycin and 1×HAT (Sigma, CRL P-7185). After 1-2 weeks, cells are cultured in medium in which the HAT is replaced with HT. Individual wells are then screened by ELISA for human anti-TMEM16A monoclonal IgG antibodies. Once extensive hybridoma growth occurred, medium is monitored usually after 10-14 days. The antibody secreting hybridomas are replated, screened again and, if still positive for human IgG, anti-TMEM16A monoclonal antibodies are subcloned at least twice by limiting dilution. The stable subclones are then cultured in vitro to generate small amounts of antibody in tissue culture medium for further characterization.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% Origen® (IGEN), 4 mM L-glutamine, 1 mM sodium pyruvate, 5 mM HEPES, 0:055 mM 2-mercaptoethanol, 50 units/ml penicillin, 50 μg/ml streptomycin, 50 μg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using an extinction coefficient of 1.43. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, 1985 Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. 1990 Methods in Enzymology 185, Academic Press, San Diego, Calif.). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665; and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood, 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in Kaufman and Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

4. Assays for Identifying and Functional Analysis of the TMEM16A Binding Molecules Standard assays to evaluate the ability of molecules to bind to TMEM16A of various species, and particular epitopes of TMEM16A, are known in the art, including, for example, ELISAs and western blots. Determination of whether an TMEM16A binding molecule binds to a specific epitope of TMEM16A (e.g., KLIRYKLKLQ) can employ a peptide epitope competition assay. For example, a TMEM16A binding molecule is incubated with a peptide corresponding to a TMEM16A epitope of interest (e.g., KLIRYKLKLQ) at saturating concentrations of peptide. The preincubated TMEM16A binding molecule is tested for binding to immobilized TMEM16A, e.g., by Biacore® analysis. Inhibition of TMEM16A binding by preincubation with the peptide indicates that the TMEM16A binding molecule binds to the peptide epitope. Binding kinetics also can be assessed by standard assays known in the art, such as by Biacore® analysis or apparent binding by FACS analysis. Assays to evaluate the effects of TMEM16A binding molecules on functional properties of TMEM16A are described in further detail below.

Accordingly, an TMEM16A binding molecule that "inhibits" one or more of these TMEM16A functional properties (e.g., biochemical, cellular, physiological or other biological activities, or the like), as determined according to methodologies known to the art and described herein, will be understood to produce a statistically significant decrease in the particular functional property relative to that seen in the absence of the binding molecule (e.g., when a control molecule of irrelevant specificity is present). A TMEM16A binding molecule that inhibits TMEM16A activity effects such a statistically significant decrease by at least 5% of the measured parameter. In certain embodiments, an antagonizing antibody or other TMEM16A binding molecule may produce a decrease in the selected functional property of at least 10%, 20%, 30%, or 50% compared to control.

In some embodiments, TMEM16A inhibition is determined by measuring levels of proteins or protein stability functioning in the same pathway as that of TMEME16A. In other embodiments, biological, physiological, and/or morphological changes indicate that the TMEM16A binding molecule inhibits TMEM16A, e.g., to inhibit the growth of a tumor cell or to induce apoptosis in a tumor cell including genes associated with the TMEM16A colocalized in the 11q13 amplicon, i.e., Cyclin D, FGF19, FGF3, FGF4, EMS1, PPFIA1, FADD.

Contrarily, a TMEM16A binding molecule that agonizes or promotes TMEM16A activity effectuates such a statistically significant increase by at least 5% of the measured parameter. In certain embodiments, an agonizing antibody or other TMEM16A binding molecule may produce an increase in the selected functional property of at least 10%, 20%, 30%, or 50% compared to control.

In some embodiments, TMEM16A inhibition is determined by measuring expression or stability levels of downstream mRNA messages or proteins in TMEM16A pathway. These pathways include all oncogenic transcription factors or oncogenic pathways upstream or downstream of TMEM16A, including but are not limited to, the transcription factors KLF4, cMYC, RAS, Raf, p53, and E1A or the IL4 signaling transduction pathway known to up-regulate TMEM16A expression levels. In other embodiments, biological, physiological, and/or morphological changes indicate that the TMEM16A binding molecule inhibits TMEM16A function, e.g., blockade of calcium activated chloride channel activity as measured by patch clamp.

Amplification and/or overexpression of TMEM16A (in GIST and ESCC) suggests a functional role in cancer. Loss of function of TMEM16A either by blockade with an antagonistic antibody, toxin conjugated antibody, synthetic small molecule, or siRNA will lead to a loss of viability of tumor cells. In vitro assays including measurement of ATP using a luciferase reporter, growth in soft agar, growth in a colony formation assay, or growth as a spheroid are all cell based viability read outs of TMEM16A activity.

Transgenic animals and cell lines are particularly useful in screening antibodies or antibody-drug conjugates (ADC) that have potential as prophylactic or therapeutic treatments of diseases or disorders involving overexpression of tumor-associated antigens, e.g. TMEM16A. Screening for a useful antibody or ADC may involve administering candidate antibody or ADC over a range of doses to the transgenic animal, and assaying at various time points for the effect(s) of the antibody or ADC on the disease or disorder being evaluated. Alternatively, or additionally, the drug can be administered prior to or simultaneously with exposure to an inducer of the disease, if applicable. Candidate antibody or ADC may be screened serially and individually, or in parallel under medium or high-throughput screening format. The rate at which antibody or ADC may be screened for utility for prophylactic or therapeutic treatments of diseases or disorders is limited only by the rate of synthesis or screening methodology, including detecting/measuring/analysis of data.

The cytotoxic or cytostatic activity of an antibody-drug conjugate (ADC) can be measured by: exposing mammalian cells having tumor-associated antigens (e.g., TMEM16A) to the antibody of the ADC in a cell culture medium; culturing the cells for a period from about 6 hours to about 5 days; and measuring cell viability. Cell-based in vitro assays may be used to measure viability, e.g. proliferation (IC50), cytotoxicity (EC50), and induction of apoptosis (caspase activation) of the ADC.

5. Compositions Comprising TMEM16A Binding Molecules

The invention provides pharmaceutical compositions comprising the present anti-TMEM16A antibodies or antigen-binding molecules formulated together with a pharmaceutically acceptable carrier. The compositions can additionally contain other therapeutic agents that are suitable for treating or preventing a given disorder. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, intranasal, inhalational, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The antibodies (or antigen binding molecules) of the invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present invention. Applicable methods for formulating the antibodies and determining appropriate dosing and scheduling can be found, for example, in *Remington: The Science and Practice of Pharmacy*, $21^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia,* 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of the anti-TMEM16A antibody is employed in the pharmaceutical compositions of the invention. The anti-TMEM16A antibodies are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

6. Uses and Methods of the Invention

The TMEM16A binding molecules described herein have in vitro and in vivo diagnostic and therapeutic utilities. For example, these molecules can be administered to cells in culture, e.g. in vitro or in vivo, or in a subject, to treat, prevent or diagnose a variety of disorders. TMEM16A binding molecules are particularly suitable for treating human patients suffering from cancer, infectious diarrhea (bacterial or viral), or sepsis. An agonist antibody or low molecular weight inhibitor approach could be employed for dry eye or dry mouth (Sjogren's syndrome).

In one embodiment, TMEM16A binding molecules can be used to diagnose, ameliorate the symptoms of, protect against, and treat cancer by binding to ECD2 of TMEM16A. Cancers which are amenable to treatment by the administration of the TMEM16A binding molecules of the invention include but are not limited to gastrointestinal cancer, gastrointestinal stromal tumor, esophageal squamous cell carcinoma, oral squamous cell carcinoma, head and neck cancer, and all other cancers relating to 11q13 amplification.

In a related fashion, the TMEM16A binding molecules of the invention are capable of inhibiting the growth of a tumor cell, or of inducing apoptosis in, or inhibiting angiogenesis of, a tumor cell. For example, to inhibit tumor growth, a tumor cell can be contacted with an anti-TMEM16A antibody, antibody fragment thereof, an antibody drug conjugate, or other TMEM16A binding molecules.

When TMEM16A binding molecules are administered together with another agent, the two can be administered sequentially in either order or simultaneously. In some embodiments, a TMEM16A binding molecule is administered to a subject who is also receiving therapy with a second agent. Said second agent can be a chemotherapeutic, in the case of cancers. A combination therapy regimen may be additive, or it may produce synergistic results (e.g., increases in apoptosis of cancer cells greater than expected for the combined use of the two agents).

In one embodiment, the TMEM16A binding molecules of the invention can be used to detect levels of TMEM16A. This can be achieved, for example, by contacting a sample (such as an in vitro sample) and a control sample with the TMEM16A binding molecule under conditions that allow for the formation of a complex between the binding molecule and TMEM16A. Any complexes formed between the molecule and TMEM16A are detected and compared in the sample and the control. For example, standard detection methods, well known in the art, such as ELISA and flow cytometric assays, can be performed using the compositions of the invention.

Accordingly, in one aspect, the invention further provides methods for detecting the presence of TMEM16A (e.g., human TMEM16A) in a sample, or measuring the amount of TMEM16A, comprising contacting the sample, and a control sample, with an TMEM16A binding molecule (e.g., an antibody) of the invention, under conditions that allow for formation of a complex between the antibody or portion thereof and TMEM16A. The formation of a complex is then detected, wherein a difference in complex formation between the sample compared to the control sample is indicative of the presence of TMEM16A in the sample.

Also within the scope of the invention are kits consisting of the compositions of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

EXAMPLES

The following examples are offered to illustrate, but not to limit the claimed invention.

Mouse, rat and human TMEM16A have been sequenced and found to be almost identical (>98%) across the whole protein. TMEM16A has been reported to be expressed in mouse epithelia, lung and kidney, acinar cells of the pancreas and submandibular gland.

The human derived, pharangeal squamous cell carcinoma FaDu cell-line (HTB-43) was grown in Eagles Minimum Essential Medium. The cervical epithelial adenocarcinoma HeLa cell-line (CCL-2) was also cultured in Eagles Minimum Essential Medium. TE-11 is an esophageal squamous cell carcinoma. GIST882 cells are derived from a patient with metastatic GIST tumor. GISTs are classified most often as smooth muscle tumors, however, contemporary histopathological criteria, particularly expression of the c-KIT receptor tyrosine kinase (CD117), enable true non-myogenic GISTs to be discriminated from other gastrointestinal mesenchymal tumors. Sequencing of the c-KIT gene has revealed activating mutations in many GISTs, a key role for c-KIT in GIST pathogenesis is supported by the finding that some kindreds with an autosomal dominant pattern of multiple primary GISTs have germline c-KIT activating mutations. The mechanisms of GIST c-KIT activation appear to be varied, as suggested by the finding of oncogenic mutations in the extracellular, juxtamembrane, and kinase domains. The relevance of c-KIT signaling in the pathobiology of GIST has been established using a GIST cell line, GIST882, from a patient with metastatic GIST. The GIST882 cell line is of stromal origin and grows in perpetuity in cell culture. Both the primary GIST and the GIST882 cell line expressed a c-KIT allele with an exon 13 missense mutation, resulting in a single amino acid substitution, K642E, in the proximal part of the split tyrosine kinase domain. The K642E c-KIT oncoprotein, in GIST882 cell lysates, had constitutive kinase activity. In addition, wild-type c-KIT transcripts were not detected in either the primary tumor or in GIST882, and GIST882 did not proliferate in response to supplemental stem cell factor (SCF). Cytogenetic characterization revealed monosomy of chromosomes 14 and 22 in the GIST882 cell line and primary tumor.

Te-11 and GIST882 cells were cultured in RPMI medium (Invitrogen). All media was supplemented with 10% fetal bovine serum (FBS), and cells grown in flasks at 37° C. in a humidified incubator with 5% $CO_2$.

Example 1

Antibody Generation

The peptide sequence KLIRYLKLKQ was used to raise a mouse monoclonal antibody (5E2D1, which is an IgG1 antibody). FIG. 1 highlights where the peptide sequence was directed. SP31 (ab64085) Abcam is a rabbit monoclonal antibody against human TMEM16A. We have mapped SP-31 binding to the 2nd extracellular domain using peptide blocking experiments and western blotting. BV-10 (ab65970) Abcam is also a rabbit monoclonal antibody against human TMEM16A. TMEM16A was detected using a rabbit polyclonal anti-TMEM16A antibody (BV10 ab65970). The immunogen is a synthetic peptide from the C-terminus of human TMEM16A.

Figure 7:
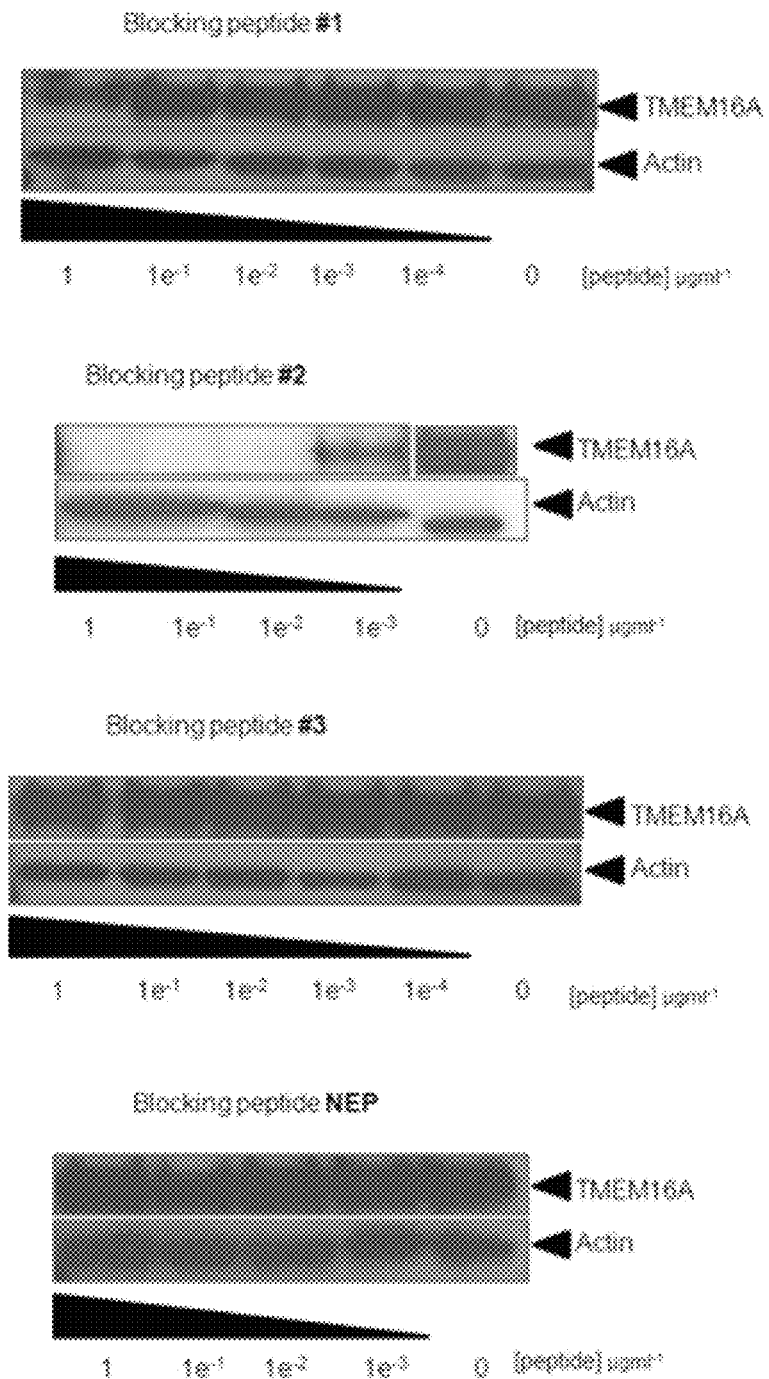
FIG. 7 shows SP31 ab64085 recognizes a different epitope within ECD2 of TMEM16A, as compared to 5E2D1.

In addition, a second rabbit antibody to human TMEM16A ("SP31 ab64085") was tested. Three blocking peptides were generated: Peptide #1 has the amino acid sequence of EEAVKDHPRAEYEARVLEKSLK (SEQ ID NO:4), Peptide #2 has the amino acid sequence of DHEECVKRKQRYEVDYNLE (SEQ ID NO:5); and Peptide #3 has the amino acid sequence of KEKVLMVELFMREEQDK (SEQ ID NO:6). Peptides #1 and #3 did not reduce SP31 ab64085 signal by western blot. Pre-incubation with peptide 2 effectively blocked SP31 at 1e-2 ugml-1 (see FIG. 7). This data suggests SP31 ab64085 recognizes amino acids 724-742 present in the second extracellular loop (ECD2) of TMEM16A.

Example 2

Differential Expression in Cancer Versus Normal Tissues

Two commercial antibodies (SP-31 and BV-10) recognizing TMEM16A were tested against a panel of normal and tumor tissue arrays. Formalin fixed paraffin embedded arrays were obtained from Pantomics. Antibody concentrations were optimized prior to testing the arrays. An array (MN0341) containing 33 types of normal tissue was used to determine expression in patient critical tissues such as liver, kidney, heart. Multiple tumor arrays were tested containing tissue specific normal and cancerous tissue. Tumor arrays tested included GIST481, a gastrointestinal stromal tumor array containing 24 univolved and GIST tissues. Other arrays were tested from esophagus (ESC241), stomach (STC961) and colon (COC481).

Addition arrays were obtained from Biomax and tested with SP-31, BV-10 and isotype control. Arrays tested included FDA955 normal tissue array, GIST881, gastrointestinal stromal tumor array, and HN802 a head and neck tumor array.

Figure 2:
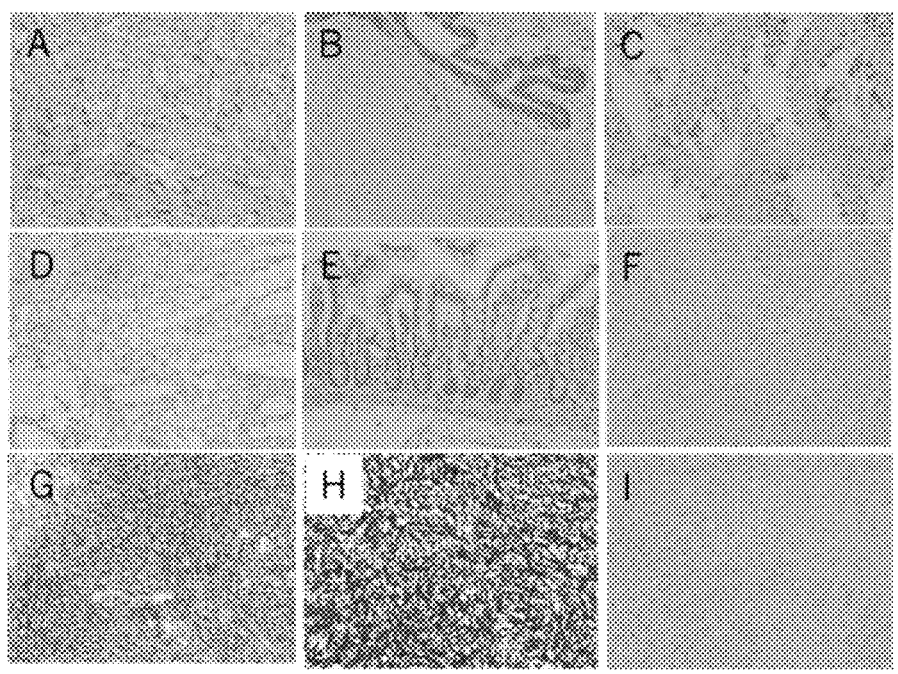
FIG. 2 shows representative images from Pantomics tissue array. Images show staining of formalin fixed paraffin embedded tissues incubated with SP-31 ab64085 (a rabbit antibody against human TMEM16A). (A) normal spleen; (B) normal breast; (C) normal testes; (D) normal stomach; (E) normal small intestine; (F) normal heart; (G) malignant stromal tumor stomach; (H) malignant stromal tumor small intestine; and (I) normal liver.

In the Pantomics array MN0341 of 33 normal tissues showed very limited staining with TMEM16A both with the BV-10 antibody and the SP-31 antibody. There was some staining evident in the fallopian tube, spleen, testes and breast duct tissue. No staining was evident in any other tisues in the array which included: cerebellum, small intestine, lung, pituatary gland, umbilical cord, cerebral cortex, stomach, liver, parathyroid adenoma, spinal chord, tonsil, bone marrow kidney, skin, thymus, uterus, bladder, heart, ovary, prostate, adrenal glands, thyroid, colon, lymph node, placenta, startified muscle, and urethra. Similar results were obtained with BV-10 and SP-31. SP-31 was used for all subsequent immunohistochemistry. FIG. 2 shows TMEM16A expression is elevated in tumor samples relative to normal tissue.

Example 3

TMEM16A is Localized on the Cell Surface

Cell surface localization of TMEM16A was tested in two different assay systems, formalin fixed paraffin embedded (FFPE) cell line pellets and expression of the TMEM16A-GFP tagged ORF in Hela cells.

Formalin Fixed Paraffin Embedded Cell Line Pellets:

Gastrointestinal stromal tumor cell lines GIST882 were cultured, embedded in paraffin and formalin fixed. The resulting pellets were incubated with either SP-31 or IgG isotype control. The detailed method is described herein: cells were grown to 80% confluence in T150 flasks, media was aspirated and cells rinsed twice with 40 ml of sterile PBS. Cells were initially fixed for 10 min using 40 ml of 10% neutral buffered formalin. Cells were then detached using a scraper and collected into a 50 ml conical tube. Fixation was continued for an additional two hours. Post fixation, cells were pelleted by centrifugation for 5 min at 1200 rpm and formalin removed by aspiration. A range of 0.5-1 ml of warmed histogel (65° C.) was added to the cells and mixed gently by pipetting up and down. The cells and warmed gel are transferred into a 7 mm×7 mm tissue mold and cooled to room temp. Using a spatula, the gel matrix was removed and placed in a tissue cassette between two sponges. The cassette was passed through a graded series of alcohol (70%, 80%, 95%, and 100% ethanol), xylene, and paraffin under vacuum infiltration for twenty minutes each step, using a tissue processor. The cassette was then removed from the processor and the gel matrix containing the cells was embedded in paraffin wax and ready for sectioning. Sections were cut onto glass slides and stained either with SP-31 or IgG isotype control.

Figure 3:
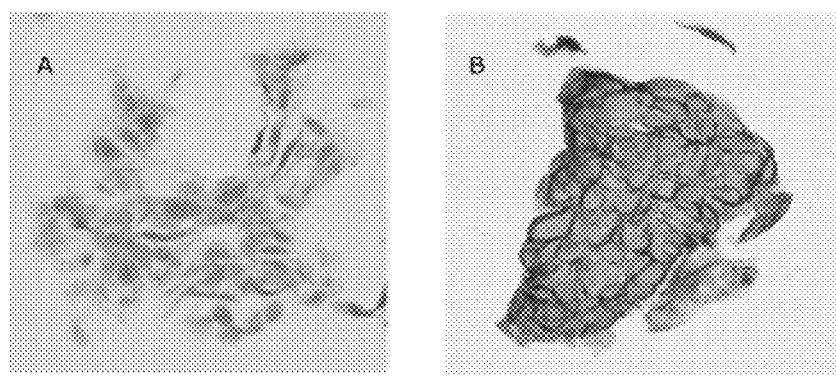
FIG. 3 shows cell surface localization of endogenous TMEM16A in GIST882 cells. (A) cell surface staining with IgG isotype control; (B) cell surface staining with SP-31 ab64085.

Result: The isotype control yielded no staining, following incubation with secondary antibody. As shown in FIG. 3, the SP-31 antibody recognizing TMEM16A showed very strong membranous staining, demonstrating high levels of TMEM16A localization on the surface of GIST882 cells.

Cell Surface Localization of TMEM16A-GFP:

Hela cells have undectable levels of TMEM16A mRNA and protein as measured by RTPCR and Western blot, respectively. Hela cells were transfected with a TMEM16A-GFP fusion protein. The cDNA ORF (NM_018043.4) was obtained in a plasmid vector pCMV6-AC-gfp (Origene). The cDNA is GFP tagged at the C-terminus to allow quantification of the expressed protein. As a control, the vector only was used. Hela-TMEM16A-GFP stable cell line and Hela-vector only-GFP stable cell line was built following transfection with Fugene HD and selection using geneticin 400 ug/ml.

Figure 4:
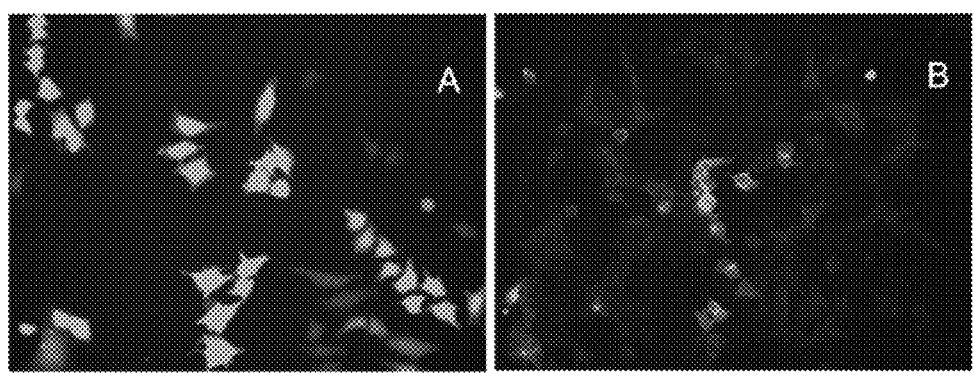
FIG. 4 shows cell surface localization of over-expressed TMEM16A in Hela cells. Hela stable cell lines were generated expressing either (A) pCMV6-AC-GFP vector only; or (B) pCMV6-AC-TMEM16A-GFP. Expression of TMEM16A is restricted to the plasma membrane of the cells. Cells imaged at 20× magnification.

Result: Stable Hela cell lines expressing either TMEM16A-GFP tagged ORF the vector only were generated following Fugene transfection, selction with geneticin and rounds of cell sorting for GFP positive cells. These cells were seen to be pure populations stably expressing either TMEM16A or vector control. Fluorescence light microscopy shows that the vector control GFP signal is evident throughout the cells (FIG. 4(A)). In contrast TMEM16A-GFP is seen only in the cell membrane in Hela TMEM16A overexpressing cells (FIG. 4(B)).

Example 4

Target-Antibody Internalization

GIST882 cells were trypsinized and resuspended at 1×10$^6$/ml in growth medium (RPMI-1640). 1 ml of cell suspension was added to ten 5 ml BD Falcon tubes, cells were pelleted, medium aspirated and cell pellets disrupted by agitation. All subsequent washes and dilutions were in phosphate buffered saline plus 1% fetal bovine serum. Neat 5E2D1 tissue culture supernatant or isotype control (1 µml-1) was added for 30 min at 4° C. Cells were washed and tubes were placed in a 37° C. water bath for 0 min, 15 min, 30 min, 1 hour or 4 hours. Following this incubation step 1:500 dilution of anti-mouse Alexa635 (Invitrogen) was added for 30 min at 4° C. Cells were washed again and returned to 4° C. prior to analysis on a BD LSRII.

Figure 5:
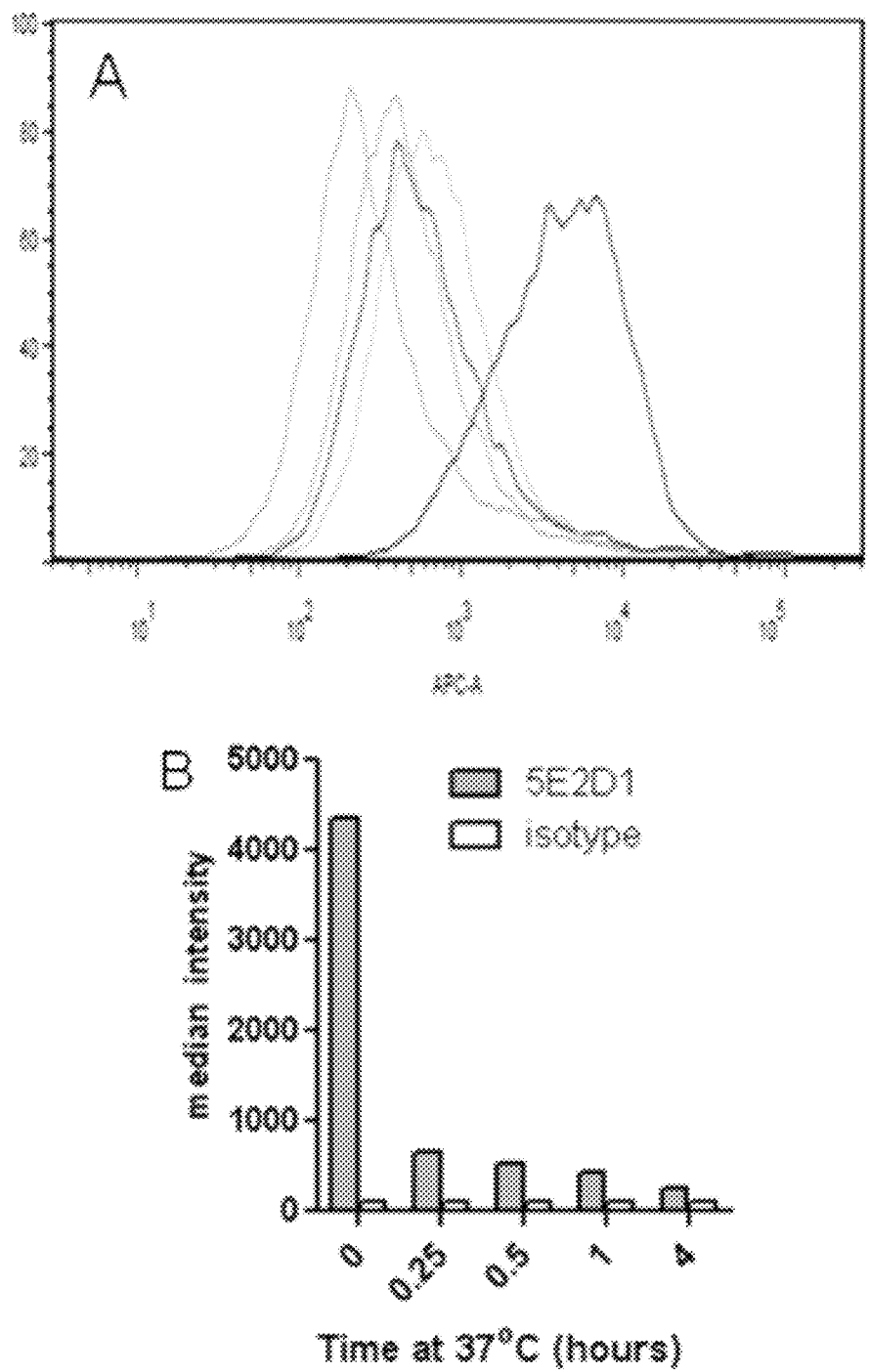
FIG. 5 shows internalization of TMEM16A following 5E2D1 binding in GIST882 cells. 5E2D1 reacts strongly to GIST882 cells in flow cytometry assays. (A) shows the raw flow cytometry data. The median fluorescence intensities were calculated and are shown graphed (B).

5E2D1 antibody recognizes an extracellular portion of the TMEM16A molecule. Using TMEM16A expressing GIST882 cells, we were able to demonstrate good staining by flow cytometry using an APC secondary antibody (SP-31 and BV-10 did not work in flow cytometry assays) as shown in FIG. 5 (B) time 0. The normal flow cytometry staining protocol was adjusted to assess internalization of TMEM16A/ 5E2D1. Instead of the usual add primary, wash, add secondary, wash then read, for internalization we add primary, wash, incubate at 37° C. for 15 minutes to 4 hours, add secondary, wash then read. We were able to demonstrate a rapid loss of TMEM16A signal within 15 minutes of cells being placed at 37° C. This is indicative of 5ED1 labeled TMEM16A being internalized prior to addition of the secondary antibody.

Example 5

Sensitivity of Cancer Models to Free Toxin Payload

In order to evaluate the effect of a toxin on model cell lines GIST882 cells were incubated with a dose series of Saporin. Cell viability was assessed after 72 hours incubation using Cell Titer Glo (Promega). Induction of targeted cell killing was assessed using 5E2D1 and a Saporin conjugated anti-mouse secondary antibody (Advanced Targeting systems). The detailed experimental protocol was followed according to the manufacturer's instructions. Briefly 10,000 cells were seeded into wells in of a 96-well white-walled clear-bottomed plate in 100 μl growth medium. After 24 hours Saporin and antibody additions were made. Growth medium was aspirated and replaced with 50 μl of fresh growth medium. Primary and secondary antibody dilutions were prepared and pre-incubated for 30 min at room temperature before addition to the cells. To each well a final dose of 200 ng/ml of secondary Saporin conjugated antibody was added either Mab-zap (kit-04-25) or goat-IgG-zap control. To the secondary was added a ten-fold dose series of primary antibody, dilutions starting either at 100 nM of primary isotype control.

The CellTiter-Glo® (CTG) Assay (Promega) is a homogeneous method of determining cell viability based on quantitation of ATP levels. The assay was used according to the manufacture's instructions. Briefly substrate and buffer were combined and mixed to form the reagent. Cells were plated in assay medium in costar 96 well white plates (Corning #3903) were left in a humidified 37° C. incubator for the desired assay lengthh. To a total volume of 100 ul of cells plus treatment an equal volume of CTG assay reagent was added. CTG luminescence was read after 10 minutes incubation at room temperature. Luminescence was measured using an EnVision™ 2100 multi-label reader (PerkinElmer™)

Figure 6:
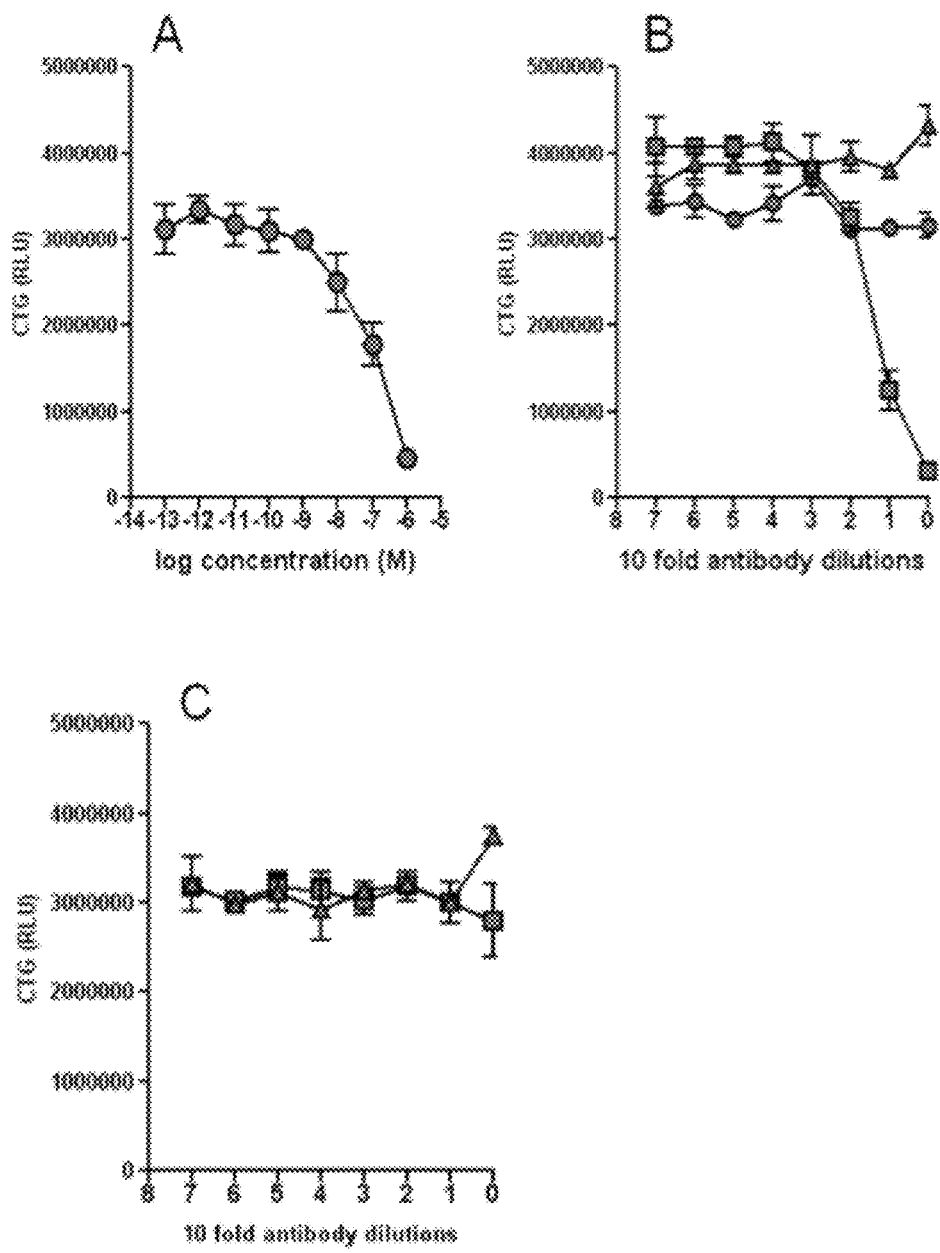
FIG. 6 shows effect of Saporin and antibody conjugated Saporin on GIST882 cells. (A) demonstrates cell killing in the presence of free Saporin. (B) shows the effects of antibody Saporin with different primary antibodies. (C) shows the effects of isotype control (filled triangle) or 5E2D1 (filled square) incubated with control goat-zap antibody conjugated Saporin.

Results:

GIST882 cells were incubated with a ten-fold dilution series of Saporin, with a top dose of 1 μM. Unconjugated Saporin effectively killed GIST882 cells at 1 μM with an $IC_{50}$ of approximately 100 nM FIG. 6(A).

To assess the effect of specific antibody mediated killing secondary antibody was prepared to a final dose of 200 ng per ml in all wells. The primary antibodies were prepared to generate a 10 fold serial dilution across the plate.

5E2D1 was able to induce killing of GIST882 cells in the presence of Saporin conjugated mouse-zap at the highest doses. No killing was observed when the same experiment was set up with equivalent doses of 5E2D1 plus saporin conjugated gaot-zap were used (FIG. 6(C)). Killing was specifically induced only in the presence of 5E2D1 and species specific secondary, ruling out a non-specific effect of 5E2D1 only.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. An isolated antibody or antigen binding fragment thereof that specifically binds to (1) a peptide consisting of SEQ ID NO:3; and (2) the extracellular domain 2 (ECD2) of transmembrane protein 16A (TMEM16).

2. The antibody or antigen binding fragment of claim 1, wherein the fragment is an Fab fragment, an Fab' fragment, an F(ab')2, or an Fv fragment.

3. The isolated antibody of antigen binding fragment of claim 1, wherein said antibody is a monoclonal antibody.

4. The isolated antibody or antigen binding fragment of claim 3, wherein said antibody is a humanized or human antibody.

5. The isolated antibody or antigen binding fragment of claim 3, wherein said antibody is a chimeric antibody.

6. The isolated antibody or antigen binding fragment of claim 1, wherein said antibody is a diabody or multivalent antibody.

7. The isolated antibody or antigen binding fragment of claim 1, wherein said antibody or antigen binding fragment is further linked to an anti-cancer agent.

8. The isolated antibody or antigen binding fragment of claim 7, wherein said anti-cancer agent is a cytotoxic agent.

9. A pharmaceutical composition comprising the isolated antibody or antigen binding fragment of claim 1.

10. The isolated antibody or antigen binding fragment of claim 1, wherein said antibody or antigen binding fragment is internalized into the cell upon binding to the ECD2.

* * * * *

SEQUENCE LISTING

```
<160> NUMBER OF SEQ ID NOS: 6

<210> SEQ ID NO 1
<211> LENGTH: 1008
<212> TYPE: PRT
<213> ORGANISM: Homo sapiens

<400> SEQUENCE: 1

Met Arg Val Asn Glu Lys Tyr Ser Thr Leu Pro Ala Glu Asp Arg Ser
1               5                   10                  15

Val His Ile Ile Asn Ile Cys Ala Ile Glu Asp Ile Gly Tyr Leu Pro
            20                  25                  30

Ser Glu Gly Thr Leu Leu Asn Ser Leu Ser Val Asp Pro Asp Ala Glu
        35                  40                  45

Cys Lys Tyr Gly Leu Tyr Phe Arg Asp Gly Arg Arg Lys Val Asp Tyr
    50                  55                  60

Ile Leu Val Tyr His His Lys Arg Pro Ser Gly Asn Arg Thr Leu Val
65                  70                  75                  80

Arg Arg Val Gln His Ser Asp Thr Pro Ser Gly Ala Arg Ser Val Lys
                85                  90                  95

Gln Asp His Pro Leu Pro Gly Lys Gly Ala Ser Leu Asp Ala Gly Ser
            100                 105                 110
```

-continued

Gly Glu Pro Pro Met Asp Tyr His Glu Asp Asp Lys Arg Phe Arg Arg
            115                 120                 125

Glu Glu Tyr Glu Gly Asn Leu Leu Glu Ala Gly Leu Glu Leu Glu Arg
        130                 135                 140

Asp Glu Asp Thr Lys Ile His Gly Val Gly Phe Val Lys Ile His Ala
145                 150                 155                 160

Pro Trp Asn Val Leu Cys Arg Glu Ala Glu Phe Leu Lys Leu Lys Met
                165                 170                 175

Pro Thr Lys Lys Met Tyr His Ile Asn Glu Thr Arg Gly Leu Leu Lys
            180                 185                 190

Lys Ile Asn Ser Val Leu Gln Lys Ile Thr Asp Pro Ile Gln Pro Lys
        195                 200                 205

Val Ala Glu His Arg Pro Gln Thr Met Lys Arg Leu Ser Tyr Pro Phe
    210                 215                 220

Ser Arg Glu Lys Gln His Leu Phe Asp Leu Ser Asp Lys Asp Ser Phe
225                 230                 235                 240

Phe Asp Ser Lys Thr Arg Ser Thr Ile Val Tyr Glu Ile Leu Lys Arg
                245                 250                 255

Thr Thr Cys Thr Lys Ala Lys Tyr Ser Met Gly Gln Gly Glu Gly Arg
            260                 265                 270

Lys Lys Asp Ser Ala Leu Leu Ser Lys Arg Lys Cys Gly Lys Tyr
        275                 280                 285

Gly Ile Thr Ser Leu Leu Ala Asn Gly Val Tyr Ala Ala Ala Tyr Pro
    290                 295                 300

Leu His Asp Gly Asp Tyr Asn Gly Glu Asn Val Glu Phe Asn Asp Arg
305                 310                 315                 320

Lys Leu Leu Tyr Glu Glu Trp Ala Arg Tyr Gly Val Phe Tyr Lys Tyr
                325                 330                 335

Gln Pro Ile Asp Leu Val Arg Lys Tyr Phe Gly Glu Lys Ile Gly Leu
            340                 345                 350

Tyr Phe Ala Trp Leu Gly Val Tyr Thr Gln Met Leu Ile Pro Ala Ser
        355                 360                 365

Ile Val Gly Ile Ile Val Phe Leu Tyr Gly Cys Ala Thr Met Asp Glu
    370                 375                 380

Asn Ile Pro Ser Met Glu Met Cys Asp Gln Arg His Asn Ile Thr Met
385                 390                 395                 400

Cys Pro Leu Cys Asp Lys Thr Cys Ser Tyr Trp Lys Met Ser Ser Ala
                405                 410                 415

Cys Ala Thr Ala Arg Ala Ser His Leu Phe Asp Asn Pro Ala Thr Val
            420                 425                 430

Phe Phe Ser Val Phe Met Ala Leu Trp Ala Ala Thr Phe Met Glu His
        435                 440                 445

Trp Lys Arg Lys Gln Met Arg Leu Asn Tyr Arg Trp Asp Leu Thr Gly
    450                 455                 460

Phe Glu Glu Glu Glu Glu Ala Val Lys Asp His Pro Arg Ala Glu Tyr
465                 470                 475                 480

Glu Ala Arg Val Leu Glu Lys Ser Leu Lys Lys Glu Ser Arg Asn Lys
                485                 490                 495

Glu Lys Arg Arg His Ile Pro Glu Glu Ser Thr Asn Lys Trp Lys Gln
            500                 505                 510

Arg Val Lys Thr Ala Met Ala Gly Val Lys Leu Thr Asp Lys Val Lys
        515                 520                 525

Leu Thr Trp Arg Asp Arg Phe Pro Ala Tyr Leu Thr Asn Leu Val Ser
    530                 535                 540

```
Ile Ile Phe Met Ile Ala Val Thr Phe Ala Ile Val Leu Gly Val Ile
545                 550                 555                 560

Ile Tyr Arg Ile Ser Met Ala Ala Ala Leu Ala Met Asn Ser Ser Pro
                565                 570                 575

Ser Val Arg Ser Asn Ile Arg Val Thr Val Thr Ala Thr Ala Val Ile
            580                 585                 590

Ile Asn Leu Val Val Ile Ile Leu Leu Asp Glu Val Tyr Gly Cys Ile
            595                 600                 605

Ala Arg Trp Leu Thr Lys Ile Glu Val Pro Lys Thr Glu Lys Ser Phe
610                 615                 620

Glu Glu Arg Leu Ile Phe Lys Ala Phe Leu Leu Lys Phe Val Asn Ser
625                 630                 635                 640

Tyr Thr Pro Ile Phe Tyr Val Ala Phe Lys Gly Arg Phe Val Gly
                645                 650                 655

Arg Pro Gly Asp Tyr Val Tyr Ile Phe Arg Ser Phe Arg Met Glu Glu
                660                 665                 670

Cys Ala Pro Gly Gly Cys Leu Met Glu Leu Cys Ile Gln Leu Ser Ile
                675                 680                 685

Ile Met Leu Gly Lys Gln Leu Ile Gln Asn Asn Leu Phe Glu Ile Gly
690                 695                 700

Ile Pro Lys Met Lys Lys Leu Ile Arg Tyr Leu Lys Leu Lys Gln Gln
705                 710                 715                 720

Ser Pro Pro Asp His Glu Glu Cys Val Lys Arg Lys Gln Arg Tyr Glu
                725                 730                 735

Val Asp Tyr Asn Leu Glu Pro Phe Ala Gly Leu Thr Pro Glu Tyr Met
                740                 745                 750

Glu Met Ile Ile Gln Phe Gly Phe Val Thr Leu Phe Val Ala Ser Phe
                755                 760                 765

Pro Leu Ala Pro Leu Phe Ala Leu Leu Asn Asn Ile Ile Glu Ile Arg
                770                 775                 780

Leu Asp Ala Lys Lys Phe Val Thr Glu Leu Arg Arg Pro Val Ala Val
785                 790                 795                 800

Arg Ala Lys Asp Ile Gly Ile Trp Tyr Asn Ile Leu Arg Gly Ile Gly
                805                 810                 815

Lys Leu Ala Val Ile Ile Asn Ala Phe Val Ile Ser Phe Thr Ser Asp
                820                 825                 830

Phe Ile Pro Arg Leu Val Tyr Leu Tyr Met Tyr Ser Lys Asn Gly Thr
                835                 840                 845

Met His Gly Phe Val Asn His Thr Leu Ser Ser Phe Asn Val Ser Asp
                850                 855                 860

Phe Gln Asn Gly Thr Ala Pro Asn Asp Pro Leu Asp Leu Gly Tyr Glu
865                 870                 875                 880

Val Gln Ile Cys Arg Tyr Lys Asp Tyr Arg Glu Pro Pro Trp Ser Glu
                885                 890                 895

Asn Lys Tyr Asp Ile Ser Lys Asp Phe Trp Ala Val Leu Ala Ala Arg
                900                 905                 910

Leu Ala Phe Val Ile Val Phe Gln Asn Leu Val Met Phe Met Ser Asp
                915                 920                 925

Phe Val Asp Trp Val Ile Pro Asp Ile Pro Lys Asp Ile Ser Gln Gln
930                 935                 940

Ile His Lys Glu Lys Val Leu Met Val Glu Leu Phe Met Arg Glu Glu
945                 950                 955                 960

Gln Asp Lys Gln Gln Leu Leu Glu Thr Trp Met Glu Lys Glu Arg Gln
                965                 970                 975
```

```
Lys Asp Glu Pro Pro Cys Asn His His Asn Thr Lys Ala Cys Pro Asp
            980                 985                 990

Ser Leu Gly Ser Pro Ala Pro Ser His Ala Tyr His Gly Gly Val Leu
            995                 1000                1005

<210> SEQ ID NO 2
<211> LENGTH: 4876
<212> TYPE: PRT
<213> ORGANISM: Homo sapiens

<400> SEQUENCE: 2

Ala Ala Ala Gly Gly Cys Gly Gly Cys Cys Gly Gly Cys Thr Gly
1               5                   10                  15

Gly Cys Gly Thr Cys Cys Ala Ala Gly Thr Thr Cys Cys Thr Gly Ala
            20                  25                  30

Cys Cys Ala Gly Gly Cys Gly Cys Gly Gly Gly Cys Cys Gly Gly Cys
            35                  40                  45

Cys Cys Gly Cys Gly Gly Ala Cys Cys Ala Gly Cys Ala Gly Cys
50                  55                  60

Cys Gly Gly Gly Thr Gly Cys Gly Gly Cys Gly Cys Gly Ala Thr
65                  70                  75                  80

Cys Gly Gly Cys Cys Cys Gly Ala Gly Ala Gly Cys Thr Cys
            85                  90                  95

Ala Gly Gly Cys Gly Cys Cys Cys Cys Gly Cys Ala Thr Cys
            100                 105                 110

Gly Ala Gly Cys Gly Cys Gly Cys Gly Gly Cys Cys Gly Gly Gly
            115                 120                 125

Cys Gly Gly Cys Cys Ala Gly Gly Cys Gly Gly Cys Gly Gly
            130                 135                 140

Gly Cys Gly Gly Ala Gly Cys Gly Gly Ala Gly Cys Gly Gly
145                 150                 155                 160

Cys Cys Ala Cys Gly Thr Cys Cys Cys Gly Gly Cys Gly Gly
            165                 170                 175

Cys Cys Thr Gly Gly Gly Cys Gly Cys Gly Gly Gly Ala Gly Gly
            180                 185                 190

Cys Cys Cys Gly Gly Cys Cys Cys Thr Gly Cys Gly Ala Gly
            195                 200                 205

Cys Gly Cys Gly Cys Cys Cys Gly Ala Ala Cys Thr Gly
            210                 215                 220

Cys Gly Gly Thr Cys Thr Cys Cys Gly Cys Cys Gly Cys Ala Gly
225                 230                 235                 240

Ala Gly Gly Cys Cys Gly Cys Cys Gly Gly Gly Cys Cys Gly Thr
            245                 250                 255

Gly Gly Ala Thr Gly Gly Gly Ala Gly Gly Gly Cys Gly Cys Gly
            260                 265                 270

Cys Cys Gly Cys Cys Gly Gly Cys Gly Gly Thr Cys Cys Cys Ala
            275                 280                 285

Gly Cys Gly Cys Ala Cys Ala Gly Gly Cys Gly Gly Cys Ala Cys
            290                 295                 300

Gly Ala Thr Gly Ala Gly Gly Thr Cys Ala Ala Cys Gly Ala Gly
305                 310                 315                 320

Ala Ala Gly Thr Ala Cys Thr Cys Gly Ala Cys Gly Cys Thr Cys
            325                 330                 335

Cys Gly Gly Cys Cys Gly Ala Gly Ala Cys Cys Gly Cys Ala Gly
            340                 345                 350
```

-continued

Cys Gly Thr Cys Cys Ala Cys Ala Thr Cys Ala Thr Cys Ala Ala Cys
355 360 365

Ala Thr Cys Thr Gly Cys Gly Cys Cys Ala Thr Cys Gly Ala Gly Gly
370 375 380

Ala Cys Ala Thr Cys Gly Gly Cys Thr Ala Cys Cys Thr Gly Cys Cys
385 390 395 400

Gly Thr Cys Cys Gly Ala Gly Gly Gly Cys Ala Cys Gly Cys Thr Gly
405 410 415

Cys Thr Gly Ala Ala Cys Thr Cys Cys Thr Thr Ala Thr Cys Thr Gly
420 425 430

Thr Gly Gly Ala Cys Cys Cys Thr Gly Ala Thr Gly Cys Cys Gly Ala
435 440 445

Gly Thr Gly Cys Ala Ala Gly Thr Ala Thr Gly Gly Cys Cys Thr Gly
450 455 460

Thr Ala Cys Thr Thr Cys Ala Gly Gly Gly Ala Cys Gly Gly Cys Cys
465 470 475 480

Gly Gly Cys Gly Cys Ala Ala Gly Gly Thr Gly Gly Ala Cys Thr Ala
485 490 495

Cys Ala Thr Cys Cys Thr Gly Gly Thr Gly Thr Ala Cys Cys Ala Thr
500 505 510

Cys Ala Cys Ala Ala Gly Ala Gly Gly Cys Cys Cys Thr Cys Gly Gly
515 520 525

Gly Cys Ala Ala Cys Cys Gly Gly Ala Cys Cys Cys Thr Gly Gly Thr
530 535 540

Cys Ala Gly Gly Ala Gly Gly Gly Thr Gly Cys Ala Gly Cys Ala Cys
545 550 555 560

Ala Gly Cys Gly Ala Cys Ala Cys Cys Cys Cys Cys Thr Cys Thr Gly
565 570 575

Gly Gly Gly Cys Thr Cys Gly Cys Ala Gly Cys Gly Thr Cys Ala Ala
580 585 590

Gly Cys Ala Gly Gly Ala Cys Cys Ala Cys Cys Cys Cys Cys Thr Gly
595 600 605

Cys Cys Gly Gly Gly Cys Ala Ala Gly Gly Gly Gly Gly Cys Gly Thr
610 615 620

Cys Gly Cys Thr Gly Gly Ala Thr Gly Cys Ala Gly Gly Cys Thr Cys
625 630 635 640

Gly Gly Gly Gly Gly Ala Gly Cys Cys Cys Cys Cys Gly Ala Thr Gly
645 650 655

Gly Ala Cys Thr Ala Cys Cys Ala Cys Gly Ala Gly Gly Ala Thr Gly
660 665 670

Ala Cys Ala Ala Gly Cys Gly Cys Thr Thr Cys Cys Gly Cys Ala Gly
675 680 685

Gly Gly Ala Gly Gly Ala Gly Thr Ala Cys Gly Ala Gly Gly Gly Cys
690 695 700

Ala Ala Cys Cys Thr Cys Cys Thr Gly Gly Ala Gly Gly Cys Gly Gly
705 710 715 720

Gly Cys Cys Thr Gly Gly Ala Gly Cys Thr Gly Gly Ala Gly Cys Gly
725 730 735

Gly Gly Ala Cys Gly Ala Gly Gly Ala Cys Ala Cys Thr Ala Ala Ala
740 745 750

Ala Thr Cys Cys Ala Cys Gly Gly Ala Gly Thr Cys Gly Gly Gly Thr
755 760 765

Thr Thr Gly Thr Gly Ala Ala Ala Ala Thr Cys Cys Ala Thr Gly Cys
770 775 780

-continued

Cys Cys Cys Cys Thr Gly Gly Ala Ala Cys Gly Thr Gly Cys Thr Gly
785                 790                 795                 800

Thr Gly Cys Ala Gly Ala Gly Ala Gly Cys Cys Gly Ala Gly Thr
        805                 810                 815

Thr Thr Cys Thr Gly Ala Ala Cys Thr Gly Ala Ala Gly Ala Thr
        820                 825                 830

Gly Cys Cys Gly Ala Cys Gly Ala Ala Gly Ala Gly Ala Thr Gly
        835                 840                 845

Thr Ala Cys Cys Ala Cys Ala Thr Thr Ala Thr Gly Ala Gly Ala
        850                 855                 860

Cys Cys Cys Gly Thr Gly Gly Cys Cys Thr Cys Cys Thr Gly Ala Ala
865                 870                 875                 880

Ala Ala Ala Ala Ala Thr Cys Ala Ala Cys Thr Cys Thr Gly Thr Gly
                885                 890                 895

Cys Thr Cys Cys Ala Gly Ala Ala Ala Thr Cys Ala Cys Ala Gly
        900                 905                 910

Ala Thr Cys Cys Cys Ala Thr Cys Cys Ala Gly Cys Cys Ala Ala
        915                 920                 925

Ala Gly Thr Gly Gly Cys Thr Gly Ala Gly Cys Ala Cys Ala Gly Gly
        930                 935                 940

Cys Cys Cys Cys Ala Gly Ala Cys Cys Ala Thr Gly Ala Ala Gly Ala
945                 950                 955                 960

Gly Ala Cys Thr Cys Thr Cys Thr Ala Thr Cys Cys Cys Thr Thr
        965                 970                 975

Cys Thr Cys Cys Cys Gly Gly Gly Ala Gly Ala Ala Gly Cys Ala Gly
        980                 985                 990

Cys Ala Thr Cys Thr Ala Thr Thr Thr Gly Ala Cys Thr Thr Gly Thr
        995                 1000                1005

Cys Thr Gly Ala Thr Ala Ala Gly Gly Ala Thr Thr Cys Cys Thr
        1010                1015                1020

Thr Thr Thr Thr Cys Gly Ala Cys Ala Gly Cys Ala Ala Ala Ala
        1025                1030                1035

Cys Cys Cys Gly Gly Ala Gly Cys Ala Cys Gly Ala Thr Thr Gly
1040                1045                1050

Thr Cys Thr Ala Thr Gly Ala Gly Ala Thr Cys Thr Thr Gly Ala
        1055                1060                1065

Ala Gly Ala Gly Ala Ala Cys Gly Ala Cys Gly Thr Gly Thr Ala
1070                1075                1080

Cys Ala Ala Ala Gly Gly Cys Cys Ala Ala Gly Thr Ala Cys Ala
        1085                1090                1095

Gly Cys Ala Thr Gly Gly Gly Cys Cys Ala Ala Gly Gly Cys Gly
1100                1105                1110

Ala Gly Gly Gly Ala Ala Gly Ala Ala Ala Gly Ala Ala Gly Gly
        1115                1120                1125

Ala Cys Thr Cys Cys Gly Cys Cys Cys Thr Thr Cys Thr Ala Ala
1130                1135                1140

Gly Thr Ala Ala Ala Ala Gly Gly Cys Gly Gly Ala Ala Ala Thr
        1145                1150                1155

Gly Thr Gly Gly Gly Ala Ala Gly Thr Ala Thr Gly Gly Cys Ala
        1160                1165                1170

Thr Cys Ala Cys Gly Ala Gly Cys Cys Thr Gly Cys Thr Gly Gly
        1175                1180                1185

Cys Cys Ala Ala Thr Gly Gly Thr Gly Thr Gly Thr Ala Cys Gly
        1190                1195                1200

-continued

```
Cys Gly Gly Cys Thr Gly Cys Ala Thr Ala Cys Cys Ala Cys
1205                1210                1215

Thr Gly Cys Ala Cys Gly Ala Thr Gly Gly Ala Gly Ala Cys Thr
1220                1225                1230

Ala Cys Ala Ala Cys Gly Gly Thr Gly Ala Ala Ala Cys Gly
1235                1240                1245

Thr Cys Gly Ala Gly Thr Thr Cys Ala Ala Cys Gly Ala Cys Ala
1250                1255                1260

Gly Ala Ala Ala Ala Cys Thr Cys Cys Thr Gly Thr Ala Cys Gly
1265                1270                1275

Ala Ala Gly Ala Gly Thr Gly Gly Gly Cys Ala Cys Gly Cys Thr
1280                1285                1290

Ala Thr Gly Gly Ala Gly Thr Thr Thr Cys Thr Ala Thr Ala
1295                1300                1305

Ala Gly Thr Ala Cys Cys Ala Gly Cys Cys Ala Thr Cys Gly
1310                1315                1320

Ala Cys Cys Thr Gly Gly Thr Cys Ala Gly Gly Ala Ala Gly Thr
1325                1330                1335

Ala Thr Thr Thr Thr Gly Gly Gly Gly Ala Gly Ala Ala Gly Ala
1340                1345                1350

Thr Cys Gly Gly Cys Thr Gly Thr Ala Cys Thr Thr Cys Gly
1355                1360                1365

Cys Cys Thr Gly Gly Cys Thr Gly Gly Gly Cys Gly Thr Gly Thr
1370                1375                1380

Ala Cys Ala Cys Cys Cys Ala Gly Ala Thr Gly Cys Thr Cys Ala
1385                1390                1395

Thr Cys Cys Cys Thr Gly Cys Thr Cys Ala Thr Cys Gly
1400                1405                1410

Thr Gly Gly Gly Ala Ala Thr Cys Ala Thr Gly Thr Cys Thr
1415                1420                1425

Thr Cys Cys Thr Gly Thr Ala Cys Gly Gly Ala Thr Gly Cys Gly
1430                1435                1440

Cys Cys Ala Cys Cys Ala Thr Gly Gly Ala Thr Gly Ala Ala Ala
1445                1450                1455

Ala Cys Ala Thr Cys Cys Cys Ala Gly Cys Ala Thr Gly Gly
1460                1465                1470

Ala Gly Ala Thr Gly Thr Gly Thr Gly Ala Cys Cys Ala Gly Ala
1475                1480                1485

Gly Ala Cys Ala Cys Ala Ala Thr Ala Thr Cys Ala Cys Cys Ala
1490                1495                1500

Thr Gly Thr Gly Cys Cys Cys Gly Cys Thr Thr Gly Cys Gly
1505                1510                1515

Ala Cys Ala Ala Gly Ala Cys Thr Gly Cys Ala Gly Cys Thr
1520                1525                1530

Ala Cys Thr Gly Gly Ala Ala Gly Ala Thr Gly Ala Gly Cys Thr
1535                1540                1545

Cys Ala Gly Cys Cys Thr Gly Cys Gly Cys Cys Ala Cys Gly Gly
1550                1555                1560

Cys Cys Cys Gly Cys Gly Cys Cys Ala Gly Cys Cys Ala Cys Cys
1565                1570                1575

Thr Cys Thr Thr Cys Gly Ala Cys Ala Ala Cys Cys Cys Cys Gly
1580                1585                1590

Cys Cys Ala Cys Gly Gly Thr Cys Thr Thr Cys Thr Thr Cys Thr
1595                1600                1605
```

-continued

```
Cys Thr  Gly Thr Cys Thr Thr  Cys Ala Thr Gly Gly  Cys Cys Cys
    1610                1615                1620

Thr Cys  Thr Gly Gly Gly Cys  Thr Gly Cys Cys Ala  Cys Cys Thr
    1625                1630                1635

Thr Cys  Ala Thr Gly Gly Ala  Gly Cys Ala Cys Thr  Gly Gly Ala
    1640                1645                1650

Ala Gly  Cys Gly Gly Ala Ala  Ala Cys Ala Gly Ala  Thr Gly Cys
    1655                1660                1665

Gly Ala  Cys Thr Cys Ala Ala  Cys Thr Ala Cys Cys  Gly Cys Thr
    1670                1675                1680

Gly Gly  Gly Ala Cys Cys Thr  Cys Ala Cys Gly Gly  Gly Cys Thr
    1685                1690                1695

Thr Thr  Gly Ala Ala Gly Ala  Gly Gly Ala Ala Gly  Ala Gly Gly
    1700                1705                1710

Ala Gly  Gly Cys Thr Gly Thr  Cys Ala Ala Gly Gly  Ala Thr Cys
    1715                1720                1725

Ala Thr  Cys Cys Thr Ala Gly  Ala Gly Cys Thr Gly  Ala Ala Thr
    1730                1735                1740

Ala Cys  Gly Ala Ala Gly Cys  Cys Ala Gly Ala Gly  Thr Cys Thr
    1745                1750                1755

Thr Gly  Gly Ala Gly Ala Ala  Gly Thr Cys Thr Cys  Thr Gly Ala
    1760                1765                1770

Ala Gly  Ala Ala Ala Gly Ala  Gly Thr Cys Cys Ala  Gly Ala Ala
    1775                1780                1785

Ala Cys  Ala Ala Ala Gly Ala  Gly Ala Ala Gly Cys  Gly Cys Cys
    1790                1795                1800

Gly Gly  Cys Ala Thr Ala Thr  Thr Cys Cys Ala Gly  Ala Gly Gly
    1805                1810                1815

Ala Gly  Thr Cys Ala Ala Cys  Ala Ala Ala Cys Ala  Ala Ala Thr
    1820                1825                1830

Gly Gly  Ala Ala Gly Cys Ala  Gly Ala Gly Gly Gly  Thr Thr Ala
    1835                1840                1845

Ala Gly  Ala Cys Ala Gly Cys  Cys Ala Thr Gly Gly  Cys Gly Gly
    1850                1855                1860

Gly Gly  Gly Thr Gly Ala Ala  Ala Thr Thr Gly Ala  Cys Thr Gly
    1865                1870                1875

Ala Cys  Ala Ala Ala Gly Thr  Gly Ala Ala Gly Cys  Thr Gly Ala
    1880                1885                1890

Cys Ala  Thr Gly Gly Ala Gly  Ala Gly Ala Thr Cys  Gly Gly Thr
    1895                1900                1905

Thr Cys  Cys Cys Ala Gly Cys  Cys Thr Ala Cys Cys  Thr Cys Ala
    1910                1915                1920

Cys Thr  Ala Ala Cys Thr Thr  Gly Gly Thr Cys Thr  Cys Cys Ala
    1925                1930                1935

Thr Cys  Ala Thr Cys Thr Thr  Cys Ala Thr Gly Ala  Thr Thr Gly
    1940                1945                1950

Cys Ala  Gly Thr Gly Ala Cys  Gly Thr Thr Thr Gly  Cys Cys Ala
    1955                1960                1965

Thr Cys  Gly Thr Cys Cys Thr  Cys Gly Gly Cys Gly  Thr Cys Ala
    1970                1975                1980

Thr Cys  Ala Thr Cys Thr Ala  Cys Ala Gly Ala Ala  Thr Cys Thr
    1985                1990                1995

Cys Cys  Ala Thr Gly Gly Cys  Cys Gly Cys Cys Gly  Cys Cys Thr
    2000                2005                2010
```

```
Thr Gly Gly Cys Cys Ala Thr Gly Ala Ala Cys Thr Cys Cys Thr
    2015                2020                2025

Cys Cys Cys Cys Cys Thr Cys Cys Gly Thr Gly Cys Gly Gly Thr
    2030                2035                2040

Cys Cys Ala Ala Cys Ala Thr Cys Cys Gly Gly Gly Thr Cys Ala
    2045                2050                2055

Cys Ala Gly Thr Cys Ala Cys Ala Gly Cys Cys Ala Cys Cys Gly
    2060                2065                2070

Cys Ala Gly Thr Cys Ala Thr Cys Ala Thr Cys Ala Ala Cys Cys
    2075                2080                2085

Thr Ala Gly Thr Gly Gly Thr Cys Ala Thr Cys Ala Thr Cys Cys
    2090                2095                2100

Thr Cys Cys Thr Gly Gly Ala Cys Gly Ala Gly Gly Thr Gly Thr
    2105                2110                2115

Ala Thr Gly Gly Cys Thr Gly Cys Ala Thr Ala Gly Cys Cys Cys
    2120                2125                2130

Gly Ala Thr Gly Gly Cys Thr Cys Ala Cys Cys Ala Ala Gly Ala
    2135                2140                2145

Thr Cys Gly Ala Gly Gly Thr Cys Cys Cys Ala Ala Ala Gly Ala
    2150                2155                2160

Cys Gly Gly Ala Gly Ala Ala Ala Ala Gly Cys Thr Thr Thr Gly
    2165                2170                2175

Ala Gly Gly Ala Gly Ala Gly Gly Cys Thr Gly Ala Thr Cys Thr
    2180                2185                2190

Thr Cys Ala Ala Gly Gly Cys Thr Thr Thr Cys Cys Thr Gly Cys
    2195                2200                2205

Thr Gly Ala Ala Gly Thr Thr Gly Thr Gly Ala Ala Thr Thr
    2210                2215                2220

Cys Cys Thr Ala Cys Ala Cys Cys Cys Cys Ala Thr Cys Thr
    2225                2230                2235

Thr Thr Thr Ala Cys Gly Thr Gly Gly Cys Gly Thr Thr Cys Thr
    2240                2245                2250

Thr Cys Ala Ala Ala Gly Gly Cys Cys Gly Gly Thr Thr Thr Gly
    2255                2260                2265

Thr Thr Gly Gly Ala Cys Gly Cys Cys Cys Gly Gly Gly Cys Gly
    2270                2275                2280

Ala Cys Thr Ala Cys Gly Thr Gly Thr Ala Cys Ala Thr Thr Thr
    2285                2290                2295

Thr Cys Cys Gly Thr Thr Cys Cys Thr Cys Cys Gly Ala Ala
    2300                2305                2310

Thr Gly Gly Ala Ala Gly Ala Gly Thr Gly Thr Gly Cys Gly Cys
    2315                2320                2325

Cys Ala Gly Gly Gly Gly Gly Cys Thr Gly Cys Cys Thr Gly Ala
    2330                2335                2340

Thr Gly Gly Ala Gly Cys Thr Ala Thr Gly Cys Ala Thr Cys Cys
    2345                2350                2355

Ala Gly Cys Thr Cys Ala Gly Cys Ala Thr Cys Ala Thr Cys Ala
    2360                2365                2370

Thr Gly Cys Thr Gly Gly Gly Ala Ala Ala Cys Ala Gly Cys
    2375                2380                2385

Thr Gly Ala Thr Cys Cys Ala Gly Ala Ala Cys Ala Ala Cys Cys
    2390                2395                2400

Thr Gly Thr Thr Cys Gly Ala Gly Ala Thr Cys Gly Gly Cys Ala
    2405                2410                2415
```

```
Thr Cys Cys Cys Gly Ala Ala Gly Ala Ala Gly Ala
    2420            2425            2430

Ala Gly Cys Thr Cys Ala Thr Cys Cys Gly Cys Thr Ala Cys Cys
    2435            2440            2445

Thr Gly Ala Ala Gly Cys Thr Gly Ala Ala Gly Cys Ala Gly Cys
    2450            2455            2460

Ala Gly Ala Gly Cys Cys Cys Cys Cys Thr Gly Ala Cys Cys
    2465            2470            2475

Ala Cys Gly Ala Gly Gly Ala Gly Thr Gly Thr Gly Thr Gly Ala
    2480            2485            2490

Ala Gly Ala Gly Gly Ala Ala Ala Cys Ala Gly Cys Gly Gly Thr
    2495            2500            2505

Ala Cys Gly Ala Gly Gly Thr Gly Gly Ala Thr Thr Ala Cys Ala
    2510            2515            2520

Ala Cys Cys Thr Gly Gly Ala Gly Cys Cys Cys Thr Thr Cys Gly
    2525            2530            2535

Cys Gly Gly Gly Cys Cys Thr Cys Ala Cys Cys Cys Cys Ala Gly
    2540            2545            2550

Ala Gly Thr Ala Cys Ala Thr Gly Gly Ala Ala Ala Thr Gly Ala
    2555            2560            2565

Thr Cys Ala Thr Cys Ala Gly Thr Thr Thr Gly Gly Cys Thr
    2570            2575            2580

Thr Cys Gly Thr Cys Ala Cys Cys Cys Thr Gly Thr Thr Thr Gly
    2585            2590            2595

Thr Cys Gly Cys Cys Thr Cys Cys Thr Cys Cys Cys Cys Cys
    2600            2605            2610

Thr Gly Gly Cys Cys Cys Ala Cys Thr Gly Thr Thr Thr Gly
    2615            2620            2625

Cys Gly Cys Thr Gly Cys Thr Gly Ala Ala Cys Ala Ala Cys Ala
    2630            2635            2640

Thr Cys Ala Thr Cys Gly Ala Gly Ala Thr Cys Cys Gly Cys Cys
    2645            2650            2655

Thr Gly Gly Ala Cys Gly Cys Cys Ala Ala Ala Ala Ala Gly Thr
    2660            2665            2670

Thr Thr Gly Thr Cys Ala Cys Thr Gly Ala Gly Cys Thr Cys Cys
    2675            2680            2685

Gly Ala Ala Gly Gly Cys Cys Gly Gly Thr Ala Gly Cys Thr Gly
    2690            2695            2700

Thr Cys Ala Gly Ala Gly Cys Cys Ala Ala Ala Gly Ala Cys Ala
    2705            2710            2715

Thr Cys Gly Gly Ala Ala Thr Cys Thr Gly Gly Thr Ala Cys Ala
    2720            2725            2730

Ala Thr Ala Thr Cys Cys Thr Cys Ala Gly Ala Gly Gly Cys Ala
    2735            2740            2745

Thr Thr Gly Gly Gly Ala Ala Gly Cys Thr Thr Gly Cys Thr Gly
    2750            2755            2760

Thr Cys Ala Thr Cys Ala Thr Cys Ala Ala Thr Gly Cys Cys Thr
    2765            2770            2775

Thr Cys Gly Thr Gly Ala Thr Cys Thr Cys Cys Thr Thr Cys Ala
    2780            2785            2790

Cys Gly Thr Cys Thr Gly Ala Cys Thr Cys Ala Thr Cys Cys
    2795            2800            2805

Cys Gly Cys Gly Cys Cys Thr Gly Gly Thr Gly Thr Ala Cys Cys
    2810            2815            2820
```

-continued

```
Thr Cys Thr Ala Cys Ala Thr Gly Thr Ala Cys Ala Gly Thr Ala
        2825                2830                2835

Ala Gly Ala Ala Cys Gly Gly Ala Cys Cys Ala Thr Gly Cys
        2840                2845                2850

Ala Cys Gly Gly Cys Thr Cys Gly Thr Cys Ala Ala Cys Cys
        2855                2860                2865

Ala Cys Ala Cys Cys Cys Cys Thr Cys Cys Thr Cys Cys Thr
        2870                2875                2880

Thr Cys Ala Ala Cys Gly Thr Cys Ala Gly Thr Gly Ala Cys Thr
        2885                2890                2895

Thr Cys Cys Ala Gly Ala Ala Cys Gly Gly Cys Ala Cys Gly Gly
        2900                2905                2910

Cys Cys Cys Cys Cys Ala Ala Thr Gly Ala Cys Cys Cys Cys
        2915                2920                2925

Thr Gly Gly Ala Cys Thr Gly Gly Gly Cys Thr Ala Cys Gly
        2930                2935                2940

Ala Gly Gly Thr Gly Cys Ala Gly Ala Thr Cys Thr Gly Cys Ala
        2945                2950                2955

Gly Gly Thr Ala Thr Ala Ala Ala Gly Ala Cys Thr Ala Cys Cys
        2960                2965                2970

Gly Ala Gly Ala Gly Cys Cys Gly Cys Cys Gly Thr Gly Gly Thr
        2975                2980                2985

Cys Gly Gly Ala Ala Ala Ala Cys Ala Ala Gly Thr Ala Cys Gly
        2990                2995                3000

Ala Cys Ala Thr Cys Thr Cys Cys Ala Ala Gly Ala Cys Thr
        3005                3010                3015

Thr Cys Thr Gly Gly Gly Cys Cys Gly Thr Cys Cys Thr Gly Gly
        3020                3025                3030

Cys Ala Gly Cys Cys Cys Gly Gly Cys Thr Gly Gly Cys Gly Thr
        3035                3040                3045

Thr Thr Gly Thr Cys Ala Thr Cys Gly Thr Cys Thr Thr Cys Cys
        3050                3055                3060

Ala Gly Ala Ala Cys Cys Thr Gly Gly Thr Cys Ala Thr Gly Thr
        3065                3070                3075

Thr Cys Ala Thr Gly Ala Gly Cys Gly Ala Cys Thr Thr Thr Gly
        3080                3085                3090

Thr Gly Gly Ala Cys Thr Gly Gly Thr Cys Ala Thr Cys Cys
        3095                3100                3105

Cys Gly Gly Ala Cys Ala Thr Cys Cys Cys Cys Ala Ala Gly Gly
        3110                3115                3120

Ala Cys Ala Thr Cys Ala Gly Cys Cys Ala Gly Cys Ala Gly Ala
        3125                3130                3135

Thr Cys Cys Ala Cys Ala Ala Gly Gly Ala Gly Ala Ala Gly Gly
        3140                3145                3150

Thr Gly Cys Thr Cys Ala Thr Gly Gly Thr Gly Gly Ala Gly Cys
        3155                3160                3165

Thr Gly Thr Thr Cys Ala Thr Gly Cys Gly Gly Gly Ala Gly Gly
        3170                3175                3180

Ala Gly Cys Ala Ala Gly Ala Cys Ala Ala Gly Cys Ala Gly Cys
        3185                3190                3195

Ala Gly Cys Thr Gly Cys Thr Gly Gly Ala Ala Ala Cys Cys Thr
        3200                3205                3210

Gly Gly Ala Thr Gly Gly Ala Gly Ala Ala Gly Gly Ala Gly Cys
        3215                3220                3225
```

-continued

```
Gly Gly Cys Ala Gly Ala Ala Gly Gly Ala Cys Gly Ala Gly Cys
        3230                3235                3240

Cys Gly Cys Cys Gly Thr Gly Cys Ala Ala Cys Cys Ala Cys Cys
        3245                3250                3255

Ala Cys Ala Ala Cys Ala Cys Cys Ala Ala Ala Gly Cys Cys Thr
        3260                3265                3270

Gly Cys Cys Cys Ala Gly Ala Cys Ala Gly Cys Thr Cys Gly
        3275                3280                3285

Gly Cys Ala Gly Cys Cys Ala Gly Cys Cys Cys Cys Ala
        3290                3295                3300

Gly Cys Cys Ala Thr Gly Cys Cys Thr Ala Cys Cys Ala Cys Gly
        3305                3310                3315

Gly Gly Gly Gly Cys Gly Thr Cys Cys Thr Gly Thr Ala Gly Cys
        3320                3325                3330

Thr Ala Thr Gly Cys Cys Ala Gly Cys Gly Gly Gly Gly Cys Thr
        3335                3340                3345

Gly Gly Gly Cys Ala Gly Gly Cys Cys Ala Gly Cys Gly Gly
        3350                3355                3360

Gly Cys Ala Thr Cys Cys Thr Gly Ala Cys Cys Gly Ala Thr Gly
        3365                3370                3375

Gly Gly Cys Ala Cys Cys Cys Thr Cys Thr Cys Cys Cys Ala Gly
        3380                3385                3390

Gly Gly Cys Ala Gly Gly Cys Gly Gly Cys Thr Thr Cys Cys Cys
        3395                3400                3405

Gly Cys Thr Cys Cys Cys Ala Cys Cys Ala Gly Gly Gly Cys Cys
        3410                3415                3420

Cys Gly Gly Thr Gly Gly Gly Thr Cys Cys Thr Gly Gly Gly Thr
        3425                3430                3435

Thr Thr Thr Cys Thr Gly Cys Ala Ala Ala Cys Ala Thr Gly Gly
        3440                3445                3450

Ala Gly Gly Ala Cys Cys Ala Cys Thr Thr Thr Cys Thr Gly Ala
        3455                3460                3465

Thr Ala Gly Gly Ala Cys Ala Thr Thr Thr Thr Cys Cys Thr Thr
        3470                3475                3480

Thr Cys Thr Thr Cys Thr Thr Thr Cys Thr Gly Thr Thr Thr Thr
        3485                3490                3495

Cys Thr Thr Thr Cys Cys Thr Thr Gly Thr Thr Thr Thr Thr Thr
        3500                3505                3510

Gly Cys Ala Cys Ala Ala Ala Gly Cys Cys Ala Thr Thr Ala Thr
        3515                3520                3525

Gly Cys Ala Gly Gly Gly Ala Ala Thr Ala Thr Thr Thr Thr Thr
        3530                3535                3540

Thr Ala Ala Thr Cys Thr Gly Thr Ala Gly Thr Ala Thr Thr Cys
        3545                3550                3555

Ala Ala Gly Ala Thr Gly Ala Ala Thr Cys Ala Ala Ala Ala Thr
        3560                3565                3570

Gly Ala Thr Gly Gly Cys Thr Gly Gly Thr Ala Ala Thr Ala Cys
        3575                3580                3585

Gly Gly Cys Ala Ala Thr Ala Ala Gly Gly Thr Ala Gly Cys Ala
        3590                3595                3600

Ala Ala Gly Gly Cys Ala Gly Gly Thr Gly Cys Thr Thr Thr Gly
        3605                3610                3615

Cys Ala Gly Ala Ala Ala Gly Ala Ala Thr Gly Cys Thr Thr Gly
        3620                3625                3630
```

-continued

Gly Ala Ala Ala Cys Thr Thr Gly Ala Gly Thr Cys Thr Cys Cys
3635                3640                3645

Cys Thr Ala Gly Ala Gly Gly Thr Gly Ala Ala Ala Gly Thr
3650                3655                3660

Gly Ala Gly Cys Ala Gly Ala Gly Gly Cys Cys Cys Gly Thr Ala
3665                3670                3675

Gly Ala Ala Ala Cys Cys Thr Cys Cys Thr Cys Thr Gly Ala
3680                3685                3690

Ala Thr Cys Cys Thr Cys Cys Thr Ala Ala Thr Cys Cys Thr
3695                3700                3705

Thr Ala Ala Gly Ala Thr Ala Gly Ala Thr Gly Cys Ala Ala Ala
3710                3715                3720

Ala Thr Gly Gly Thr Ala Ala Gly Cys Cys Gly Ala Gly Gly Cys
3725                3730                3735

Ala Thr Cys Gly Cys Gly Cys Ala Ala Ala Gly Cys Thr Gly
3740                3745                3750

Gly Thr Gly Cys Gly Ala Thr Gly Cys Thr Thr Cys Ala Gly Gly
3755                3760                3765

Gly Ala Ala Ala Ala Thr Gly Gly Ala Ala Ala Cys Cys Cys
3770                3775                3780

Ala Cys Gly Cys Ala Ala Gly Ala Ala Thr Ala Ala Thr Gly Ala
3785                3790                3795

Thr Thr Gly Ala Thr Thr Cys Cys Gly Gly Thr Thr Cys Cys Ala
3800                3805                3810

Ala Ala Ala Gly Gly Thr Gly Thr Cys Ala Cys Cys Thr Ala Cys
3815                3820                3825

Cys Thr Gly Thr Thr Thr Cys Ala Gly Ala Ala Ala Ala Gly Thr
3830                3835                3840

Thr Ala Gly Ala Cys Thr Thr Cys Cys Ala Thr Cys Gly Cys
3845                3850                3855

Cys Thr Thr Thr Thr Cys Cys Thr Thr Cys Cys Ala Thr Cys Ala
3860                3865                3870

Gly Thr Thr Gly Ala Gly Thr Gly Gly Cys Thr Gly Ala Gly Ala
3875                3880                3885

Gly Ala Gly Ala Ala Gly Thr Gly Cys Cys Thr Cys Ala Thr Cys
3890                3895                3900

Cys Cys Thr Gly Ala Gly Cys Cys Ala Cys Ala Cys Ala Gly Gly
3905                3910                3915

Gly Gly Gly Cys Gly Thr Gly Gly Gly Ala Gly Cys Ala Thr Cys
3920                3925                3930

Cys Cys Ala Gly Thr Thr Ala Thr Cys Cys Cys Thr Gly Gly Ala
3935                3940                3945

Ala Ala Gly Cys Thr Ala Gly Ala Ala Gly Gly Gly Gly Ala Cys
3950                3955                3960

Ala Gly Ala Gly Gly Thr Gly Thr Cys Cys Cys Thr Gly Ala Thr
3965                3970                3975

Thr Ala Ala Gly Cys Ala Gly Gly Ala Ala Ala Cys Ala Gly Cys
3980                3985                3990

Ala Cys Cys Cys Thr Thr Gly Gly Cys Gly Thr Cys Cys Cys Cys
3995                4000                4005

Ala Gly Cys Ala Gly Gly Cys Thr Cys Cys Cys Ala Cys Thr
4010                4015                4020

Gly Thr Cys Ala Gly Cys Cys Ala Cys Ala Cys Ala Cys Cys Thr
4025                4030                4035

-continued

Gly Cys Cys Cys Cys Cys Ala Thr Cys Ala Cys Cys Ala
    4040                4045            4050

Ala Gly Cys Cys Gly Ala Cys Cys Thr Cys Ala Gly Ala Gly Thr
    4055                4060            4065

Thr Gly Thr Thr Cys Ala Thr Cys Thr Thr Cys Cys Thr Thr Ala
    4070                4075            4080

Thr Gly Gly Gly Ala Cys Ala Ala Ala Cys Cys Gly Gly Thr
    4085                4090            4095

Thr Gly Ala Cys Cys Ala Gly Ala Ala Ala Thr Gly Gly Gly
    4100                4105            4110

Cys Ala Gly Ala Gly Ala Gly Ala Gly Ala Thr Gly Ala Cys Cys
    4115                4120            4125

Thr Gly Gly Ala Ala Gly Cys Ala Thr Thr Cys Cys Ala Cys
    4130                4135            4140

Ala Gly Ala Thr Gly Gly Thr Gly Thr Cys Ala Gly Gly Gly Thr
    4145                4150            4155

Thr Thr Cys Ala Ala Gly Ala Ala Gly Thr Cys Thr Ala Gly
    4160                4165            4170

Gly Gly Cys Thr Thr Cys Cys Ala Gly Gly Gly Thr Cys Cys
    4175                4180            4185

Cys Cys Thr Gly Gly Ala Ala Gly Cys Thr Thr Ala Gly Ala
    4190                4195            4200

Ala Thr Ala Thr Thr Thr Ala Thr Gly Gly Gly Thr Thr Thr Thr
    4205                4210            4215

Thr Thr Thr Thr Thr Cys Ala Ala Ala Thr Ala Thr Cys Ala Ala
    4220                4225            4230

Thr Thr Ala Thr Ala Thr Gly Gly Thr Ala Gly Ala Thr Thr Gly
    4235                4240            4245

Ala Gly Gly Ala Thr Thr Thr Thr Thr Thr Thr Cys Thr Gly
    4250                4255            4260

Thr Ala Gly Cys Thr Cys Ala Ala Ala Gly Gly Thr Gly Gly Ala
    4265                4270            4275

Gly Gly Gly Ala Gly Thr Thr Thr Ala Thr Thr Ala Gly Thr Thr
    4280                4285            4290

Ala Ala Cys Cys Ala Ala Ala Thr Ala Thr Cys Gly Thr Thr Gly
    4295                4300            4305

Ala Gly Ala Gly Gly Ala Ala Thr Thr Thr Ala Ala Ala Ala Thr
    4310                4315            4320

Ala Cys Thr Gly Thr Thr Ala Cys Thr Ala Cys Cys Ala Ala Ala
    4325                4330            4335

Gly Ala Thr Thr Thr Thr Thr Ala Thr Ala Ala Thr Ala Ala
    4340                4345            4350

Ala Gly Gly Cys Thr Thr Ala Thr Ala Thr Thr Thr Gly Gly
    4355                4360            4365

Thr Ala Ala Cys Ala Cys Thr Thr Cys Thr Cys Thr Ala Thr Ala
    4370                4375            4380

Thr Thr Thr Thr Thr Ala Cys Thr Cys Ala Cys Ala Gly Gly Ala
    4385                4390            4395

Ala Thr Gly Thr Cys Ala Cys Thr Gly Thr Thr Gly Gly Ala Cys
    4400                4405            4410

Ala Ala Thr Thr Ala Thr Thr Thr Thr Ala Ala Ala Ala Gly Thr
    4415                4420            4425

Gly Thr Ala Thr Ala Ala Ala Ala Cys Cys Ala Ala Gly Thr Cys
    4430                4435            4440

```
Thr Cys Ala Thr Ala Ala Ala Thr Gly Ala Thr Ala Thr Gly Ala
    4445                4450                4455

Gly Thr Gly Ala Thr Cys Thr Ala Ala Ala Thr Thr Gly Cys
    4460                4465                4470

Ala Gly Cys Ala Ala Thr Gly Ala Thr Ala Cys Thr Ala Ala Ala
    4475                4480                4485

Cys Ala Ala Cys Thr Cys Thr Cys Thr Gly Ala Ala Ala Thr Thr
    4490                4495                4500

Thr Cys Thr Cys Ala Ala Gly Cys Ala Cys Cys Ala Ala Gly Ala
    4505                4510                4515

Gly Ala Ala Ala Cys Ala Thr Cys Ala Thr Thr Thr Ala Gly
    4520                4525                4530

Cys Ala Ala Ala Gly Gly Cys Cys Ala Gly Gly Ala Gly Gly Ala
    4535                4540                4545

Ala Ala Ala Ala Thr Ala Gly Ala Ala Thr Ala Ala Ala Thr
    4550                4555                4560

Thr Thr Gly Thr Cys Thr Thr Gly Ala Ala Gly Ala Thr Cys Thr
    4565                4570                4575

Cys Ala Thr Thr Gly Ala Thr Gly Thr Gly Ala Thr Gly Thr Thr
    4580                4585                4590

Ala Cys Ala Thr Thr Cys Cys Cys Thr Thr Ala Ala Thr Cys
    4595                4600                4605

Thr Gly Cys Cys Ala Ala Cys Thr Gly Thr Gly Gly Thr Cys Ala
    4610                4615                4620

Ala Ala Gly Thr Thr Cys Ala Thr Ala Gly Gly Thr Gly Thr Cys
    4625                4630                4635

Gly Thr Ala Cys Ala Thr Thr Thr Cys Cys Ala Thr Thr Ala Thr
    4640                4645                4650

Thr Thr Gly Cys Thr Ala Ala Ala Ala Thr Cys Ala Thr Gly Cys
    4655                4660                4665

Ala Ala Thr Cys Thr Gly Ala Thr Gly Cys Thr Thr Cys Thr Cys
    4670                4675                4680

Thr Thr Thr Thr Cys Thr Cys Thr Thr Gly Thr Ala Cys Ala Gly
    4685                4690                4695

Thr Ala Ala Gly Thr Ala Gly Thr Thr Thr Gly Ala Ala Gly Thr
    4700                4705                4710

Gly Gly Gly Thr Thr Thr Thr Gly Thr Ala Thr Ala Thr Ala Ala
    4715                4720                4725

Ala Thr Ala Cys Thr Gly Thr Ala Thr Thr Ala Ala Ala Ala Ala
    4730                4735                4740

Thr Thr Ala Gly Gly Cys Ala Ala Thr Ala Cys Cys Ala Ala
    4745                4750                4755

Ala Ala Ala Thr Cys Cys Thr Thr Thr Ala Thr Gly Gly Ala
    4760                4765                4770

Ala Ala Cys Cys Ala Thr Thr Thr Thr Thr Thr Ala Ala Ala
    4775                4780                4785

Ala Ala Gly Thr Gly Ala Ala Thr Gly Thr Ala Cys Ala Cys Ala
    4790                4795                4800

Ala Ala Thr Cys Cys Ala Cys Ala Gly Ala Gly Gly Ala Cys Thr
    4805                4810                4815

Gly Thr Gly Gly Cys Thr Gly Gly Ala Cys Ala Thr Thr Cys Ala
    4820                4825                4830

Thr Cys Thr Ala Ala Ala Thr Ala Ala Ala Thr Thr Thr Gly Ala
    4835                4840                4845
```

```
Ala Thr Ala Thr Ala Cys Gly  Ala Cys Ala Cys Thr  Thr Thr Thr
    4850            4855             4860

Cys Thr  Cys Ala Cys Thr Thr  Gly Ala Ala Ala Ala   Ala
    4865             4870              4875

<210> SEQ ID NO 3
<211> LENGTH: 10
<212> TYPE: PRT
<213> ORGANISM: Homo sapiens

<400> SEQUENCE: 3

Lys Leu Ile Arg Tyr Lys Leu Lys Leu Gln
1               5                   10

<210> SEQ ID NO 4
<211> LENGTH: 22
<212> TYPE: PRT
<213> ORGANISM: homo sapien

<400> SEQUENCE: 4

Glu Glu Ala Val Lys Asp His Pro Arg Ala Glu Tyr Glu Ala Arg Val
1               5                   10                  15

Leu Glu Lys Ser Leu Lys
            20

<210> SEQ ID NO 5
<211> LENGTH: 19
<212> TYPE: PRT
<213> ORGANISM: homo sapiens

<400> SEQUENCE: 5

Asp His Glu Glu Cys Val Lys Arg Lys Gln Arg Tyr Glu Val Asp Tyr
1               5                   10                  15

Asn Leu Glu

<210> SEQ ID NO 6
<211> LENGTH: 17
<212> TYPE: PRT
<213> ORGANISM: Homo Sapiens

<400> SEQUENCE: 6

Lys Glu Lys Val Leu Met Val Glu Leu Phe Met Arg Glu Glu Gln Asp
1               5                   10                  15

Lys
```